United States Patent
Marlin et al.

(10) Patent No.: US 11,413,167 B2
(45) Date of Patent: Aug. 16, 2022

(54) PROSTHETIC JOINT WITH CAM LOCKING MECHANISM

(71) Applicant: Ossur Iceland ehf, Reykjavik (IS)

(72) Inventors: Dana Stewart Marlin, Hafnarfjordur (IS); David Sandahl, Reykjavik (IS)

(73) Assignee: Össur Iceland Ehf, Reykjavik (IS)

( * ) Notice: Subject to any disclaimer, the term of this patent is extended or adjusted under 35 U.S.C. 154(b) by 246 days.

(21) Appl. No.: 16/526,053

(22) Filed: Jul. 30, 2019

(65) Prior Publication Data
US 2020/0022822 A1     Jan. 23, 2020

Related U.S. Application Data

(63) Continuation of application No. 14/624,261, filed on Feb. 17, 2015, now Pat. No. 10,405,999.
(Continued)

(51) Int. Cl.
    *A61F 2/66*     (2006.01)
    *A61F 2/60*     (2006.01)
(Continued)

(52) U.S. Cl.
    CPC ............ *A61F 2/6607* (2013.01); *A61F 2/604* (2013.01); *A61F 2/66* (2013.01); *A61F 2/80* (2013.01);
(Continued)

(58) Field of Classification Search
    CPC .... A61F 2/604; A61F 2/64; A61F 2/66; A61F 2/6607; A61F 2/80; A61F 2002/5016;
(Continued)

(56) References Cited

U.S. PATENT DOCUMENTS

| 1,319,471 A | * | 10/1919 | Giebeler-Wanke ....... A61F 2/66 623/52 |
| 2,529,968 A | * | 11/1950 | Sartin ...................... A61F 2/66 623/52 |

(Continued)

FOREIGN PATENT DOCUMENTS

| GB | 2 161 386 | 1/1986 |
| WO | WO 1985/02536 | 6/1985 |

(Continued)

OTHER PUBLICATIONS

Child's Play Knee with Manual Lock SSK610A, http://trulife.com/all-products/prosthetics/knees/child-s-play-friction-control-knee-with-lock (Available before Feb. 18, 2014).

(Continued)

*Primary Examiner* — Christie L Bahena
(74) *Attorney, Agent, or Firm* — Knobbe, Martens, Olson & Bear, LLP

(57) ABSTRACT

A prosthetic joint can include a first attachment member and a second attachment member coupled to the first attachment member. The second attachment member can include a cylindrical chamber. The prosthetic joint can include a fixation system disposed within the cylindrical chamber comprising at least one cam. The prosthetic joint can have an unlocked configuration, wherein in the unlocked configuration the first attachment member and the second attachment member can rotate relative to each other. The prosthetic joint can have a locked configuration, wherein in the locked configuration the first attachment member is substantially prevented from rotating relative to the second attachment member.

20 Claims, 25 Drawing Sheets

Related U.S. Application Data

(60) Provisional application No. 61/941,218, filed on Feb. 18, 2014.

(51) Int. Cl.
    *A61F 2/70*      (2006.01)
    *A61F 2/80*      (2006.01)
    *A61F 2/50*      (2006.01)
    *A61F 2/68*      (2006.01)

(52) U.S. Cl.
CPC ............. *A61F 2002/5072* (2013.01); *A61F 2002/6621* (2013.01); *A61F 2002/6657* (2013.01); *A61F 2002/6854* (2013.01); *A61F 2002/701* (2013.01)

(58) Field of Classification Search
CPC ...... A61F 2002/5018; A61F 2002/5043; A61F 2002/5098; A61F 2002/6621; A61F 2002/6657; A61F 2002/6854
See application file for complete search history.

(56) References Cited

U.S. PATENT DOCUMENTS

| | | | |
|---|---|---|---|
| 2,553,830 | A | 5/1951 | Motis |
| 2,594,227 | A | 4/1952 | Smith |
| 2,749,557 | A * | 6/1956 | Riddle ............... A61F 2/66 623/50 |
| 3,871,032 | A | 3/1975 | Karas |
| 4,005,496 | A | 2/1977 | Wilkes |
| 4,206,519 | A | 6/1980 | Blatchford et al. |
| 5,156,630 | A | 10/1992 | Rappoport et al. |
| 5,226,918 | A | 7/1993 | Silagy et al. |
| 5,704,945 | A | 1/1998 | Wagner et al. |
| 5,728,175 | A | 3/1998 | Rincoe |
| 5,755,813 | A | 5/1998 | Krukenberg |
| 6,165,226 | A | 12/2000 | Wagner |
| 6,436,149 | B1 | 8/2002 | Rincoe |
| 6,610,101 | B2 | 8/2003 | Herr et al. |
| 6,645,252 | B2 | 11/2003 | Asai et al. |
| 6,827,343 | B2 | 12/2004 | Skiera |
| 7,172,630 | B2 | 2/2007 | Christensen |
| 8,717,041 | B2 | 5/2014 | Steele |
| 8,814,949 | B2 | 8/2014 | Gramnaes |
| 10,405,999 | B2 | 9/2019 | Marlin et al. |
| 2004/0111163 | A1 | 6/2004 | Bedard et al. |
| 2006/0173552 | A1 | 8/2006 | Roy |
| 2006/0195197 | A1 | 8/2006 | Clausen et al. |
| 2006/0235544 | A1 | 10/2006 | Iversen et al. |
| 2007/0050044 | A1 | 3/2007 | Haynes et al. |
| 2007/0299544 | A1 | 12/2007 | Dunlap et al. |
| 2008/0203798 | A1 | 8/2008 | Kienke et al. |
| 2008/0281427 | A1 | 11/2008 | Shen |
| 2008/0312752 | A1 * | 12/2008 | Miller ............... A61F 2/66 623/55 |
| 2009/0171470 | A1 | 7/2009 | Bisinger et al. |
| 2010/0030343 | A1 | 2/2010 | Hansen et al. |
| 2012/0136458 | A1 | 5/2012 | Martin |
| 2012/0245707 | A1 | 9/2012 | Osgyan |
| 2012/0303135 | A1 | 11/2012 | Vo |
| 2013/0268093 | A1 | 10/2013 | Gilbert et al. |
| 2016/0278947 | A1 * | 9/2016 | Martin ............... A61B 5/4851 |

FOREIGN PATENT DOCUMENTS

| | | |
|---|---|---|
| WO | WO 2012/077141 | 6/2012 |
| WO | WO 2012/166853 | 12/2012 |
| WO | WO 2015/126849 | 8/2015 |

OTHER PUBLICATIONS

Extended European Search Report for European Patent Application No. 15751804.4, dated Sep. 27, 2017.
International Preliminary Report on Patentability for International Application No. PCT/US2015/016206, in 8 pages, dated Aug. 23, 2016.
International Search Report and Written Opinion for PCT/US2015/016206 dated Jul. 23, 2015, in 17 pages.
Invitation to Pay Additional Search Fees for International Application No. PCT/US2015/016206, dated May 15, 2015 in 2 pages.
Seattle Safety Knee SSK603 / SSK605, http://trulife.com/all-products/prosthetics/knees/seattle-safety-knee (Available before Feb. 18, 2014).
Seattle Single Axis Locking Knee SSK608, http://trulife.com/all-products/prosthetics/knees/seattle-single-axis-locking-knee (Available before Feb. 18, 2014).

* cited by examiner

PROSTHETIC JOINT WITH CAM LOCKING MECHANISM

Any and all applications for which a foreign or domestic priority claim is identified in the Application Data Sheet as filed with the present application are hereby incorporated by reference under 37 CFR 1.57. For example, this application is a continuation of U.S. application Ser. No. 14/624,261, filed Feb. 17, 2015, and titled PROSTHETIC JOINT WITH CAM LOCKING MECHANISM, which claims the priority benefit of U.S. Provisional Application No. 61/941,218, filed Feb. 18, 2014, and titled PROSTHETIC JOINT WITH DUAL CAM LOCKING MECHANISM, the entire disclosure of each of which is hereby incorporated by reference in its entirety for all purposes and forms a part of this specification.

BACKGROUND

Field

The present application relates to prosthetic feet, prosthetic knees, and other prosthetic devices having cams, and more particularly to prosthetic feet, prosthetic knees, and other prosthetic devices having one or more cams and allowing for changes in the angular orientation of a joint by selectively locking and unlocking the joint.

Description of the Related Art

In the field of prosthetics, particularly prosthetic feet and prosthetic knees, it is desirable to provide a high level of functionality with reliable performance. Further, as each user is different, it is desirable to provide a prosthesis that can be adapted to the particular needs of each individual user.

The prior art includes many hydraulic valve-controlled, multi-component joints. However, there is a need for a simple and robust mechanical joint that allows for selective adjustment of the angular orientation of the joint.

SUMMARY

In some embodiments, a possible advantage of the locking mechanism disclosed herein over the prior art include that the locking mechanism is a simple, intuitive, mechanical mechanism. The locking mechanism can advantageously have few moving parts, making it robust and cost-effective, as well as reducing the likelihood of wear damage during use, thereby extending the life of the joint. The prosthetic joint can be incorporated into any type of lower extremity joint, such as the ankle or knee. Further, the prosthetic joint can be incorporated into upper extremity joints.

Particularly in the area of prosthetic feet, it can be desirable for the heel height to be adjustable, while having a locked configuration during movement (e.g., while the user is walking). Throughout the gait cycle and in other activities such as stance, it can be desirable to provide a prosthesis that provides ample stability under load. Further, it can be desirable for a prosthetic foot to be freely adjustable to suit a user's preferences. For instance, the user may adjust the orientation of the prosthetic foot depending on activity level.

Of particular importance to foot prosthetics, the heel height of the prosthesis can be adjusted to match the orientation of the natural foot or the natural foot in footwear. For instance, for female amputees, the orientation of the prosthetic foot can be adjusted to match the heel height of the natural foot in footwear. This adjustability could provide the female amputee with the option to wear a variety of footwear on the natural foot, from ballet flats to stiletto heels, while allowing the prosthetic foot to match the heel height.

Turning now to the area of knee prosthetics, it can be desirable for the knee orientation to be adjustable, while having a locked configuration during movement. It can be desirable for the knee to hold the set angle under load such as during stance but to be freely repositionable in a variety of different orientations by the user. Repositioning may be needed, for instance, depending on the activity level of the amputee or the terrain (e.g., while the user is sitting down).

The adjustability of the prosthetic joint can be simple and intuitive. In some embodiments, the adjustability of the prosthetic joint can be actuated by a simple mechanical feature (e.g. buttons, lever, turnkey, brake wire, etc.). It can be desirable for the prosthetic joint to be locked and unlocked on demand (e.g., when selectively actuated by the user). Further, it can be desirable for the prosthetic joint to be adjustable to an individual who may have various weights, heights, stride lengths, etc.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

In some embodiments, a prosthetic joint is provided. The prosthetic joint can include a first attachment member and a second attachment member movably coupled to the first attachment member. The second attachment member can include a cylindrical chamber. The prosthetic joint can include a fixation system disposed within the cylindrical chamber comprising at least one cam and at least one actuator. The at least one actuator can be configured to move the at least one cam into or out of contact with the cylindrical chamber. The prosthetic joint can have an unlocked configuration when the at least one actuator moves the at least one cam out of contact with the cylindrical chamber such that the first and second attachment members are free to rotate relative to each other. The prosthetic joint can have a locked configuration when the at least one actuator moves the at least one cam into contact with the cylindrical chamber such that the first and second attachment members are inhibited from rotating relative to each other.

In some embodiments, the at least one cam comprises a first cam and a second cam. In some embodiments, the first cam does not align with the second cam in the locked configuration. In some embodiments, the first cam aligns with the second cam in the unlocked configuration. In some embodiments, the at least one actuator comprises at least two springs, wherein the at least two springs bias the first cam away from the second cam, in the locked configuration. In some embodiments, the at least one actuator comprises a first button and a second button, wherein the first button engages the first cam and the second button engages the second cam to align the cams in the unlocked configuration. In some embodiments, the at least one actuator comprises a turnkey configured to be rotated between a first position having a first dimension wherein the cams are aligned and out of contact with the cylindrical chamber, and a second position having a second dimension different than the first dimension wherein the cams are unaligned and in contact with the cylindrical chamber. In some embodiments, the at least one actuator comprises at least one linear member engaged with the second cam, the at least one linear member configured to pull the second cam toward the first cam to move the prosthetic joint to the unlocked configuration. In some embodiments, the at least one actuator comprises a lever configured to be rotated between a first position with a first dimension in contact with the at least one cam, and a second position with a second dimension in contact with the at least one cam, wherein the first dimension is greater than the second dimension. In some embodiments, the at least one actuator comprises at least one linear member, wherein the at least linear member pulls the at least one cam to reposition the at least one cam within the cylindrical chamber.

In some embodiments, a prosthetic joint is provided. The prosthetic joint can include a first attachment member and a second attachment member movably coupled to the first attachment member. The second attachment member can include a cylindrical chamber. The prosthetic joint can include a fixation system disposed within the cylindrical chamber comprising a first cam, a second cam, and a first cam spring associated with the first cam. The prosthetic joint can have an unlocked configuration wherein the first cam aligns with the second cam, wherein in the unlocked configuration the first attachment member and the second attachment member can rotate relative to each other. The prosthetic joint can have a locked configuration wherein the first cam does not align with the second cam, wherein in the locked configuration the first attachment member is inhibited from rotating relative to the second attachment member.

In some embodiments, the first cam spring biases the first cam into contact against the cylindrical chamber. The prosthetic joint can include a second cam spring associated with the second cam. In some embodiments, the first cam is biased by the first cam spring in a first direction, and the second cam is biased by the second cam spring in a second direction, wherein the first direction is opposite the second direction. The prosthetic joint can include an actuator with at least one positioning member, wherein depressing the at least one positioning member changes a configuration of the prosthetic joint from the locked configuration to the unlocked configuration. In some embodiments, the prosthetic joint comprises a pair of positioning members, and wherein depressing a first positioning member toward the first cam and depressing a second positioning member toward the second cam changes the configuration of the prosthetic joint from the locked configuration to the unlocked configuration.

In some embodiments, a prosthetic joint is provided. The prosthetic joint can include a first attachment member and a second attachment member movably coupled to the first attachment member. The second attachment member can include a cylindrical chamber. The prosthetic joint can include a fixation system disposed within the cylindrical chamber comprising a first cam, a second cam, and a turnkey actuator with a pin that extends through a first hole in the first cam and a second hole in the second cam. The prosthetic joint can be actuatable from an unlocked configuration where the first cam aligns with the second cam and the first and second attachment members can rotate relative to each other and a locked configuration where the first cam does not align with the second cam and the first and second attachment members are inhibited from rotating relative to each other.

In some embodiments, rotation of the turnkey changes the prosthetic joint from the unlocked configuration to the locked configuration. In some embodiments, the turnkey has a first non-constant dimension and a second constant dimension along a length of the pin, wherein actuation of the turnkey to place the first non-constant dimension in contact with the first and second cams causes the prosthetic joint to lock, and wherein actuation of the turnkey to place the second constant dimension in contact with the first and second cams causes the prosthetic joint to unlock. The prosthetic joint can include a first cam spring that biases the first cam toward the turnkey. The prosthetic joint can include a second cam spring that biases the second cam toward the turnkey.

In some embodiments, a prosthetic joint is provided. The prosthetic joint can include a first attachment member and a second attachment member movably coupled to the first attachment member. The second attachment member can include a cylindrical chamber. The prosthetic joint can include a fixation system disposed within the cylindrical chamber comprising a cam, and a lever having an engagement portion in contact with the cam. The prosthetic joint can have an unlocked configuration where the lever is positioned in a first position such that the cam does not contact the cylindrical surface such that the first and second attachment members can rotate relative to each other. The prosthetic joint can have a locked configuration where the lever is positioned in a second position such that the cam contacts the cylindrical surface so that the first and second attachment members are inhibited from rotating relative to each other.

In some embodiments, prosthetic joint changes from the unlocked configuration to the locked configuration by rotation of the lever. In some embodiments, the engagement portion has a first dimension and a second dimension, the second dimension less than the first dimension, wherein the prosthetic joint is in the locked configuration when the first dimension is in contact with the cam and moves the cam into contact with the cylindrical chamber, and wherein the prosthetic joint is in the unlocked configuration when the second dimension is in contact with the cam. In some embodiments, the cam is substantially diamond shaped.

In some embodiments, a prosthetic joint is provided. The prosthetic joint can include a first attachment member and a second attachment member movably coupled to the first attachment member. The second attachment member can include a cylindrical chamber. The prosthetic joint can include a fixation system disposed within the cylindrical chamber comprising a first cam, a second cam and a wire passing through an aperture in the first cam and coupled to the second cam. In some embodiments, actuation of the first and second cams toward each other moves the prosthetic joint to an unlocked configuration, wherein in the unlocked configuration the first attachment member and the second attachment member can rotate relative to each other. In some embodiments, wherein actuation of the first and second cams away from each other moves the prosthetic joint to a locked configuration, wherein in the locked configuration the first attachment member is substantially prevented from rotating relative to the second attachment member.

In some embodiments, actuation of the wire to pull the second cam into contact with the first cam moves the prosthetic joint to the unlocked configuration. The prosthetic joint can include a first distally extending lid and a second distally extending lid, wherein the first distally extending lid and the second distally extending lid enclose the cylindrical chamber. The prosthetic joint can include an axle, wherein the axle extends through the first distally extending lid, the first cam, the second cam, and the second distally extending lid. In some embodiments, the first cam and the second cam are interlaced along the axle.

In some embodiments, a prosthetic joint is provided with a variable height control, which allows the height to be adjusted based on the preferences of the user. In some embodiments, the variable height control is mechanically actuatable (e.g., actuated manually by a user) to vary the height of the proximal portion of the joint with respect to the distal portion of the joint (e.g., by depressing a button to align the cams or actuating a lever to align the cams). In another embodiment, the variable height control can be automatically or actively adjusted by the user (e.g., automatic adjustment of the cams, or active varying of the cam springs), e.g., based on the activity level of the user or the phase of gait cycle. In some embodiments the variable height control can be automatically adjusted based on a sensed parameter (e.g., sensed with one or more sensors on the prosthetic device).

In some embodiments, where the prosthetic device is a prosthetic foot, the prosthetic joint can be located generally at a location associated with a natural human ankle, and provide for heel height adjustment similar to that of a natural human ankle. In some embodiments, where the prosthetic device is a prosthetic knee, the prosthetic joint can be located generally at a location associated with a natural human knee, and provide for rotational adjustment similar to that of a natural human knee. In some embodiments, a prosthetic joint can have a connector configured to connect the prosthetic joint to a user or another prosthetic device. In some embodiments, the prosthetic device can be integrally formed with either the proximal portion or the distal portion of the prosthetic joint.

BRIEF DESCRIPTION OF THE DRAWINGS

These and other features, aspects, and advantages of the invention disclosed herein are described below with reference to the drawings of preferred embodiments, which are intended to illustrate and not to limit the invention. Additionally, from figure to figure, the same reference numerals have been used to designate the same components of an illustrated embodiment. The following is a brief description of each of the drawings.

DETAILED DESCRIPTION

Figure 1:
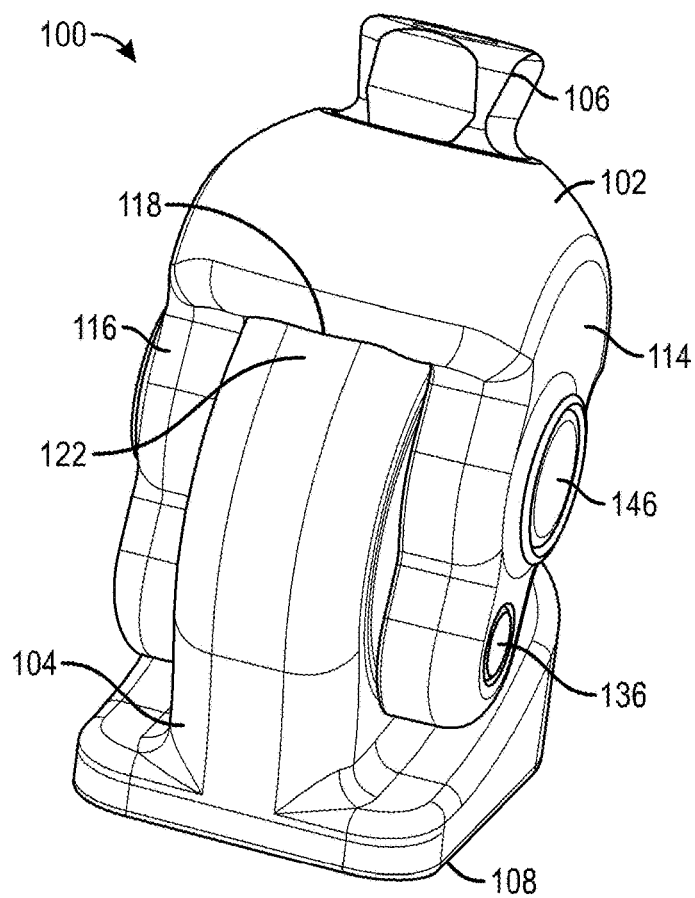
FIG. 1 is a perspective view of an embodiment of a prosthetic joint.
Figure 2:
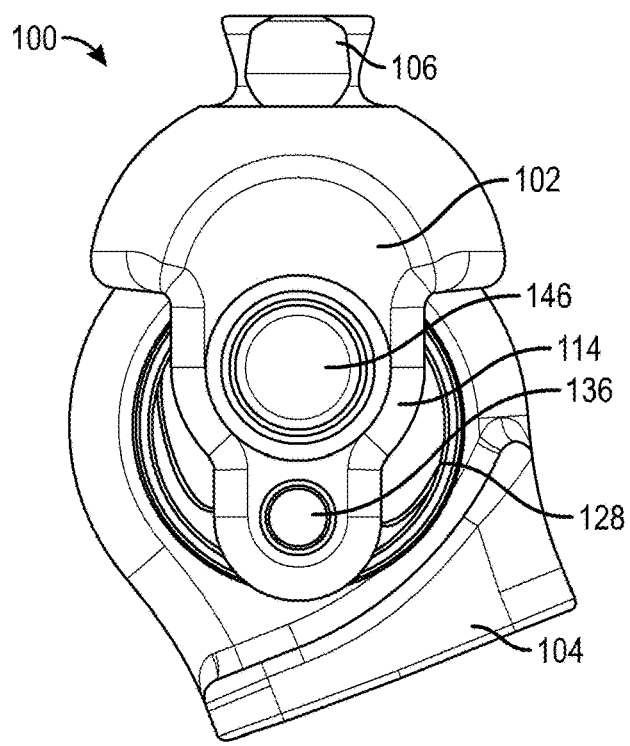
FIG. 2 is a side view of the prosthetic joint of FIG. 1 in the locked configuration.

Although certain preferred embodiments and examples are disclosed below, it will be understood by those in the art that the invention extends beyond the specifically disclosed embodiments and/or uses of the invention and obvious modifications and equivalents thereof. Thus, it is intended that the scope of the invention herein disclosed should not be limited by the particular disclosed embodiments described below.

FIGS. 1-8 depict an embodiment of a prosthetic joint 100. The prosthetic joint 100 can include a first attachment member 102 and a second attachment member 104. The prosthetic joint 100 can attach to a user or to another prosthetic device with the first attachment member 102. The prosthetic joint 100 can attach to a user or to another prosthetic device with the second attachment member 104.

The first attachment member 102 is depicted as including a first connection portion 106 shown in the illustrated embodiment as a pyramid connector. The first connection portion 106 can attach to a socket that receives a stump of a user, to another prosthetic device (e.g., a pylon), or to any other appropriate object. Further, it will be understood that the first connection portion 106 can in other embodiments include attachment features other than a pyramid connector, such as a hole and pin, a threaded hole or screw, a latch, a magnetic member, tube clamp, or other features. In some embodiments, the second attachment member 104 includes a second connection portion 108. The second connection portion 108 can include a pyramid connector, a hole and pin, a threaded hole or screw, a latch, a magnetic member, tube clamp, or other attachment features.

Figure 3:
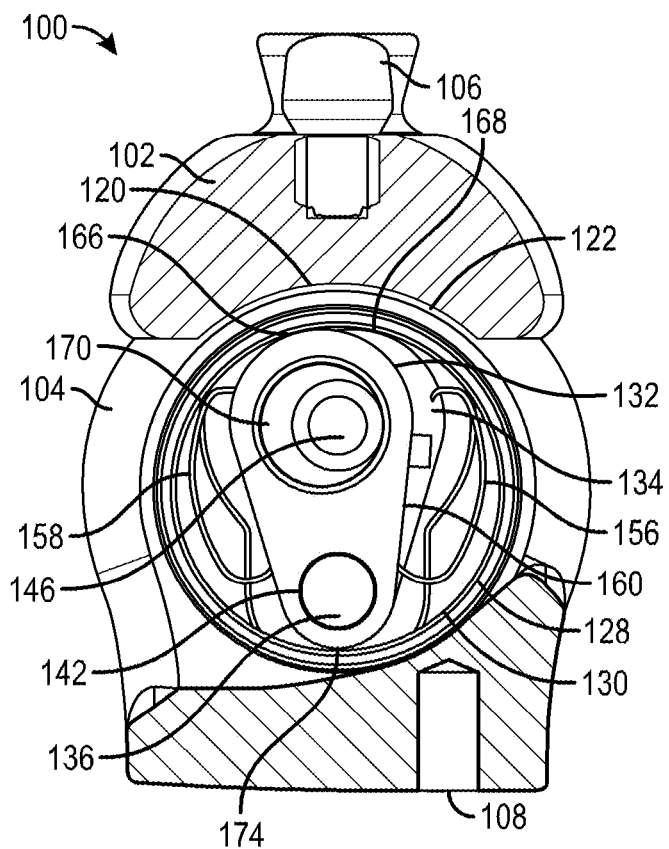
FIG. 3 is a cross-sectional side view of the prosthetic joint of FIG. 1 in the locked configuration.

In some embodiments, the first attachment member 102 can include a first distally extending arm 114 and a second distally extending arm 116. In some embodiments, the first distally extending arm 114 can be identical, substantially similar or a mirror image of the second distally extending arm 116. In between the distally extending arms 114, 116, the first attachment member 102 can have a space 118 sized to accept at least a portion of the second attachment member 104. The space 118 can permit the first attachment member 102 and the second attachment member 104 to rotate relative to each other. The space 118 can be defined by an inner surface of the first distally extending arm 114, an inner surface of the second distally extending arm 116, and an inner surface 120. The inner surface 120 can be curved or concave as shown in FIG. 3. In some embodiments, the second attachment member 104 can include a curved or convex outer surface 122. The inner surface 120 of the first attachment member 102 can provide a bearing surface for the outer surface 122 of the second attachment member 104. The inner surface 120 of the first attachment member 102 can allow the outer surface 122 of the second attachment member 104 to rotate thereon. In other embodiments, the inner surface 120 of the first attachment member 102 does not contact the outer surface 122 of the second attachment member 104.

As shown in FIGS. 1-8, the second attachment member 104 can include a cylindrical chamber 128. The cylindrical chamber 128 can define a cylindrical track 130. The prosthetic joint 100 can include one or more cams. In the illustrated embodiment, the cams include a first cam 132 and a second cam 134. FIGS. 1-8 depict the first cam 132 and the second cam 134, but one cam or a plurality of cams can be utilized. The first cam 132 and the second cam 134 are sized to fit within the cylindrical chamber 128 of the second attachment member 104. For instance, the first cam 132 and the second cam 134 together can have a smaller width than the cylindrical chamber 128. For instance, the first cam 132 and the second cam 134 can each be less than half the width of the cylindrical chamber 128. For instance, the cylindrical chamber 128 can have a diameter. The first cam 132 and the second cam 134 can have a length along their respective longitudinal axis. The length of the first cam 132 and the second cam 134 can be less than the diameter of the cylindrical chamber 128. The cylindrical chamber 128 is sized to permit the rotation of a first cam 132 and a second cam 134 therewithin, as described below.

Figure 5:
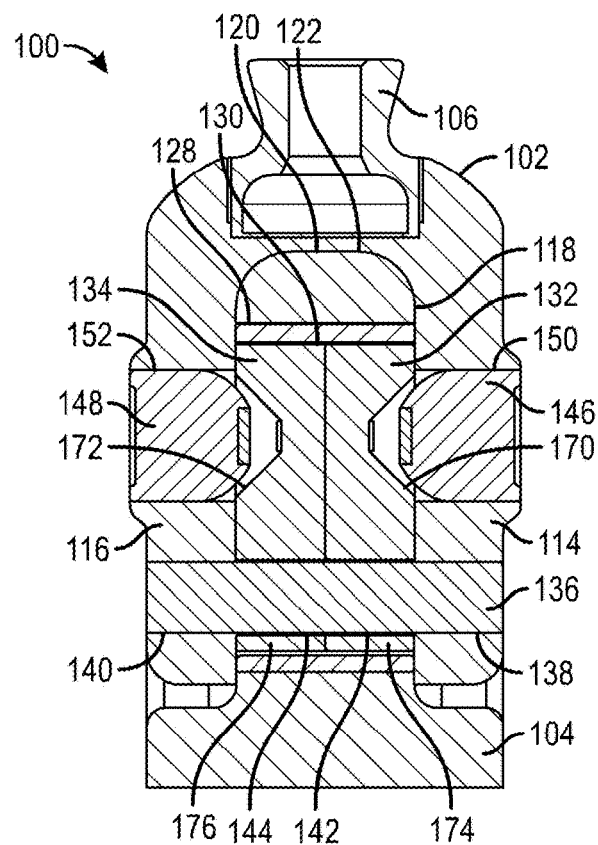
FIG. 5 is a transverse cross-sectional view of the prosthetic joint of FIG. 1 in the locked configuration.

The first attachment member 102 can provide a rotatable connection with the second attachment member 104. The first attachment member 102 can include an axle 136. The axle 136 can pass through the first distally extending arm 114 and the second distally extending arm 116. In some embodiments, the axle 136 passes through a first hole 138 in the first distally extending arm 114, as shown in FIG. 5. In some embodiments, the axle 136 passes through a second hole 140 in the second distally extending arm 116, as shown in FIG. 5. The first hole 138 can be near a distal end of the first distally extending arm 114 and the second hole 140 can be near a distal end of the second distally extending arm 116.

In some embodiments, the first cam 132 can include or define a first cam hole 142 and the second cam 134 can include or define a first cam hole 144. The axle 136 can extend through the first cam hole 142 and the second cam hole 144. The cam holes 142, 144 can each include a bushing to facilitate rotation. The first cam 132 and the second cam 134 can be rotatable with respect to the axle 136. Additional bushings or washers may be provided to prevent contact between the first cam 132 and the first distally extending arm 114, and/or to prevent contact between the second cam 134 and the second distally extending arm 116. In some embodiments, some of the cams are retained within the cylindrical chamber 128 and/or the cylindrical track 130 and other cams are not. In other embodiments, all of the cams are retained within the cylindrical chamber 128 and/or the cylindrical track 130.

The axle 136 passes through the first cam 132 and the second cam 134. In the illustrated embodiment, the axle 136 passes through a first hole 138 in the first distally extending arm 114, the first cam hole 142 in the first cam 132, the second cam hole 144 in the second cam 134, and the second hole 140 in the second distally extending arm 116 respectively. The first distally extending arm 114, the second distally extending arm 116, and the axle 136 can be rigidly coupled.

When the prosthetic joint 100 is assembled, the first attachment member 102 is coupled to the second attachment member 104 via the first cam 132 and the second cam 134. In some methods of assembly, the first cam 132 and the second cam 134 are placed within the cylindrical chamber 128 of the second attachment portion 104. The axle 136 is then passed through the first hole 138 in the first distally extending arm 114, the first cam hole 142 in the first cam 132, the second cam hole 144 in the second cam 134, and the second hole 140 in the second distally extending arm 116. The axle 136 retains the first cam 132 and the second cam 134 between the first distally extending arm 114 and the second distally extending arm 116. In some embodiments, the first cam 132 and the second cam 134 do not make contact with, abut, or otherwise touch the first distally extending arm 114 and the second distally extending arm 116. The axle 136 retains the first cam 132 and the second cam 134 in the cylindrical chamber 128. In some embodiments, the first cam 132 and the second cam 134 are retained entirely within the cylindrical chamber 128.

The prosthetic joint 100 can include one or more unlocking members. In the illustrated embodiment, the unlocking member includes a first positioning member 146 and a second positioning member 148. The first distally extending arm 114 can be associated with a first positioning member 146. The first positioning member 146 can extend at least partially through a first positioning hole 150 in the first distally extending arm 114. The first positioning member 146 can make contact with, abut, or otherwise touch the first cam 132. The first positioning member 146 can be retained within the first positioning hole 150 to permit movement along the width of the prosthetic joint 100. In some embodiments, the first positioning hole 150 restricts rotation of the first positioning member 146 disposed within.

The second distally extending arm 116 can be associated with a second positioning member 148. The second positioning member 148 can extend at least partially through a second positioning hole 152 in the second distally extending arm 116. The second positioning member 146 can make contact with, abut, or otherwise touch the second cam 134. The second positioning member 148 can be retained within the second positioning hole 152 to permit movement along the width of the prosthetic joint 100. In some embodiments, the second positioning hole 150 restricts rotation of the second positioning member 146 disposed within. In some embodiments, the first positioning member 146 is provided, the second positioning member 148 is provided or both the first positioning member 146 and the second positioning member 148 are provided.

The positioning members 146, 148 may incorporate a mechanism or feature to facilitate retention of the positioning members 146, 148 within the distally extending arms 114, 116. For instance, the positioning members 146, 148 may include a groove and the distally extending arms 114, 116 may include a corresponding tongue. The tongue and groove arrangement may retain the positioning members 146, 148 within the distally extending arms 114, 116, but allow for sliding movement of the positioning members 146, 148. For instance, the positioning members 146, 148 can include a magnet incorporated within or affixed to a surface and the distally extending arms 114, 116 can include a magnet. The magnet arrangement may retain the positioning members 146, 148 within the distally extending arms 114, 116, but allow for sliding movement of the positioning members 146, 148. For instance, the positioning members 146, 148 and/or the distally extending arms 114, 116 may include a flange, groove, protrusion, roller, detent or other feature known in the art used for retention. The first positioning member 146 and the second positioning member 148 can be configured to unlock the prosthetic joint 100 as described herein.

The first cam 132 can include a first detent 170 sized to accept at least a portion of the first positioning member 146. For instance the first detent 170 can accept a tip of the first positioning member 146. The first detent 170 can be on a surface of the first cam 132 closest to the first distally extending arm 114. The second cam 134 can include a second detent 172 sized to accept at least a portion of the second positioning member 148. For instance the second detent 172 can accept a tip of the first positioning member 148. The second detent 172 can be on a surface of the second cam 134 closest to the second distally extending arm 116. While detents 170, 172 are shown with a tapered surface, other shapes of orifices are contemplated for the detents 170, 172 such as rounded or conical.

The prosthetic joint 100 can include one or more biasing member. In the illustrated embodiment, the biasing member includes a first cam spring 156 and a second cam spring 158. The first end of the first cam spring 156 can be coupled to the first cam 132. The second end of the first cam spring 156 can make contact with, abut, or otherwise touch the cylindrical track 130. In some embodiments, the cylindrical track 130 is smooth. In other embodiments, the cylindrical track 130 includes grooves sized to accept the first cam spring 156 and/or the first cam 132. The first end of the second cam spring 158 can be coupled to the second cam 134. The second end of the second cam spring 158 can make contact with, abut, or otherwise touch the cylindrical track 130. In some embodiments, the cylindrical track 130 includes grooves sized to accept the second cam spring 158 and/or the second cam 134. The second ends of the first cam spring 156 and the second cam spring 158 are rotatable against the cylindrical track 130 of the cylindrical chamber 128. The second end of the first cam spring 156 will rotate when the first cam 132 rotates. The second end of the second cam spring 158 will rotate when the second cam 134 rotates. In other embodiments, the second ends of the first cam spring 156 and the second cam spring 26 are coupled to the cylindrical track 130.

Figure 4:
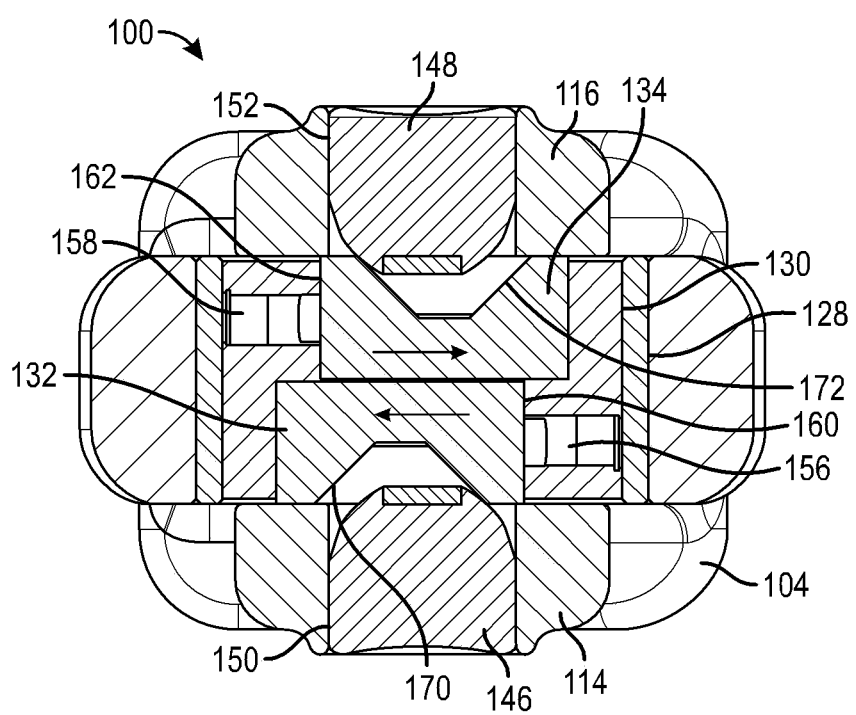
FIG. 4 is a cross-sectional top view of the prosthetic joint of FIG. 1 in the locked configuration.

The first end of the first cam spring 156 can be fixed to the first cam 132 using a fastener or any known technique in the art (e.g., pin, screw). The first end of the second cam spring 158 can be fixed to the second cam 134 using a fastener or any known technique in the art (e.g., pin, screw). The fastener for the second cam spring 158 can be the same or different type as fastener associated with the first cam spring 156. FIGS. 3-4 depict a fastener coupling the first cam spring 156 to the lateral side wall 160 of the first cam 132. FIGS. 3-4 depict a fastener coupling the second cam spring 158 to the opposed lateral side wall 162 of the second cam 134. The fasteners can be placed at any location that does not impeded rotation. In some embodiments, the first cam spring 156 only contacts the first cam 132, not the second cam 134. In some embodiments, the second cam spring 158 only contacts the second cam 134, not the first cam 132.

As shown in FIG. 4, the first cam spring 156 biases the first cam 132 in a first direction. The second cam spring 158 biases the second cam 134 in a second direction. In some embodiments, the first direction is opposite the second direction. As shown in FIG. 4, the first cam spring 156 applies a force against the lateral side wall 160 of the first cam 132 to bias the first cam 132 in a first direction. The first cam 132 can rotate about the axle 136 until an edge of the first cam 132 abuts the cylindrical track 130. The second cam spring 158 applies a force against opposed lateral side wall 162 of the second cam 134 to bias the second cam 134 in a second direction. The second cam 134 can rotate about the axle 136 until an edge of the second cam 134 abuts the cylindrical track 130. The prosthetic joint 100 is in a locked configuration when the cams 132, 134 abut the cylindrical track 130.

In a locked configuration, the first cam spring 156 and the second cam spring 158 bias the cams 132, 134 out of alignment with each other, as shown in FIGS. 3 and 4. The first cam 132 is offset with respect to the second cam 134 in a locked configuration, as shown in FIG. 3. The profile of the first cam 132 does not completely overlap the profile of the second cam 134 when viewed from the side of the prosthetic joint 100, as shown in FIG. 3. In other words, the lateral side wall 160 of the first cam 134 does not lie on the same plane as a lateral side wall of the second cam 134. The opposed lateral side wall 162 of the second cam 134 does not lie on the same plane as an opposed lateral side wall of the first cam 132.

In some embodiments, the first cam 132, the second cam 134, the first cam spring 156 associated with the first cam 132, and the second cam spring 158 associated with the second cam 134 are provided. Each cam 132, 134 has an associated cam spring 156, 158. In some embodiments, the first cam 132, the second cam 134, and the first cam spring 156 associated with the first cam 132 are provided. At least one cam does not have an associated cam spring. The first cam spring 156 can bias the first cam 132 in a first direction. The first cam spring 156 can bias the cams 132, 134 out of alignment with each other. Only one cam spring 156 is needed to bias the first cam 132 out of alignment with the second cam 134.

In some embodiments, the second cam 134 can be held stationary or otherwise fixed. The prosthetic joint 100 can include a reciprocal mechanism to control movement of the second cam 134. The reciprocal mechanism can be a shaft (not shown) which is not free to rotate. The shaft can be affixed to the second cam 134. When the first cam spring 156 applies a force on the first cam 132, only the first cam 132 rotates within the cylindrical chamber 128. The second cam 134 is constrained by the shaft. In some embodiments, the second cam 134 can be fixed relative to the cylindrical track 130, the cylindrical chamber 128, or the second distally extending arm 116. In some embodiments, the second cam 134 is affixed to the axle 136 so that the second cam 134 is not freely rotatable about the axle 136. The first cam 132 can be rotatable about the axle 136. The first cam spring 156 can bias the first cam 132 out of alignment with the second cam 134. In some embodiments, only the first cam 132 needs to be moved in order to bring the cams 132, 134 out of alignment.

The first cam spring 156 and the second cam spring 158 can be springs known in the art, such as leaf springs. The first cam spring 156 and the second cam spring 158 can include the same material, shape, and spring type or a different material, shape, and spring type. The first cam spring 156 and the second cam spring 158 can be retained within the cylindrical track 130 of the cylindrical chamber 128.

The first attachment member 102 or components thereof can include a substantially rigid material such as aluminum, steel, titanium, other metals or metallic alloys, carbon fiber, composites, or substantially rigid plastics. However, in other embodiments the first attachment member 102 can be configured to provide flexibility, potentially in multiple planes. Thus, in some embodiments the first attachment member 102 can include a more flexible material or include flexible joints between separate components of the first attachment member 102.

The second attachment member 104 or components thereof can include a substantially rigid material such as aluminum, steel, titanium, other metals or metallic alloys, carbon fiber, composites, or substantially rigid plastics. However, in other embodiments the second attachment member 104 can be configured to provide flexibility, potentially in multiple planes. Thus, in some embodiments the second attachment member 104 can include a more flexible material or include flexible joints between separate components of the second attachment member 104.

FIGS. 1-5 show the prosthetic joint 100 in the locked configuration. The first cam 132 can be aligned along a chord of the cylindrical chamber 128. The longitudinal dimension of the first cam 132 can be less than the diameter of the cylindrical chamber 128. In the locked configuration, the proximal portion 166 of the first cam 132 can make contact with, abut, or otherwise touch the cylindrical track 130 of the cylindrical chamber 128. The second cam 134 can be aligned along a chord of the cylindrical chamber 128. The longitudinal dimension of the second cam 134 can be less than the diameter of the cylindrical chamber 128. In the locked configuration, the proximal portion 168 of the second cam 134 can make contact with, abut, or otherwise touch the cylindrical track 130 of the cylindrical chamber 128.

The first cam spring 156 biases the first cam 132 into contact with the cylindrical track 130. The first cam spring 156 biases the first cam 132 in a first direction, out of alignment with the second cam 134. The second cam spring 158 biases the second cam 134 into contact with the cylindrical track 130. The second cam spring 158 biases the second cam 134 in a second direction, out of alignment with the first cam 132.

FIGS. 1-5 shows the prosthetic joint 100 in the locked configuration. In a locked configuration, the first cam spring 156 and the second cam spring 158 bias the cams 132, 134 out of alignment with each other. The first cam 132 is offset with respect to the second cam 134 in a locked configuration. As shown in FIG. 4, the first positioning member 146 can be eccentric with respect to the first detent 170. The second positioning member 148 can be similarly eccentric with respect to the second detent 172. The proximal portion 166 of the first cam 132 is in contact with the cylindrical track 130. The proximal portion 168 of the second cam 134 is in contact with the cylindrical track 130.

In some embodiments, in the locked configuration, the first cam 132 and the second cam 134 form a V-shape. At least a portion of the first cam 132 is laterally offset from the second cam 134. For instance, the proximal portion 166 of the first cam 132 can be laterally offset from the proximal portion 168 of the second cam 134. The first attachment member 102 is substantially prevented from rotating in the first direction because the first cam 132 cannot rotate further with respect to the cylindrical chamber 128 and/or the cylindrical track 130. The first attachment member 102 is substantially prevented from rotating in the second direction because the second cam 134 cannot rotate further with respect to the cylindrical chamber 128 and/or the cylindrical track 130.

In some embodiments, in the locked configuration, the first cam 132 can have one point of contact with the cylindrical track 130 of the cylindrical chamber 128. In some embodiments, the proximal portion 166 of the first cam 132 has a point of contact with the cylindrical track 130 of the cylindrical chamber 128. The distal end 174 of the first cam 132 is coupled to the axle 136. In the locked configuration, the second cam 134 has one point of contact with the cylindrical track 130 of the cylindrical chamber 128. In some embodiments, the proximal portion 168 of the second cam 134 has a point of contact with the cylindrical track 130 of the cylindrical chamber 128. The distal end 176 of the second cam 134 is coupled to the axle 136. In some embodiments, in the locked configuration, the first cam 132 can have two points of contact with the cylindrical track 130 of the cylindrical chamber 128. In some embodiments, the proximal portion 166 and the distal portion 174 of the first cam 132 each have a point of contact. In some embodiments, the proximal portion 168 and the distal portion 176 of the second cam 134 each have a point of contact.

The locked configuration can also be an equilibrium position. For prosthetic joint 100, the first positioning member 146 slides within the first positioning hole 150 in the first distally extending arm 114 until equilibrium position is reached. The first positioning member 146 slides outward, away from the first cam 132. The equilibrium position is defined as the position where the frictional force between the first positioning member 146 and the first positioning hole 150 equals the biasing force of the first cam spring 156. The second positioning member 148 also reaches an equilibrium position in the same manner as described with respect to the first positioning member 146.

Figure 6:
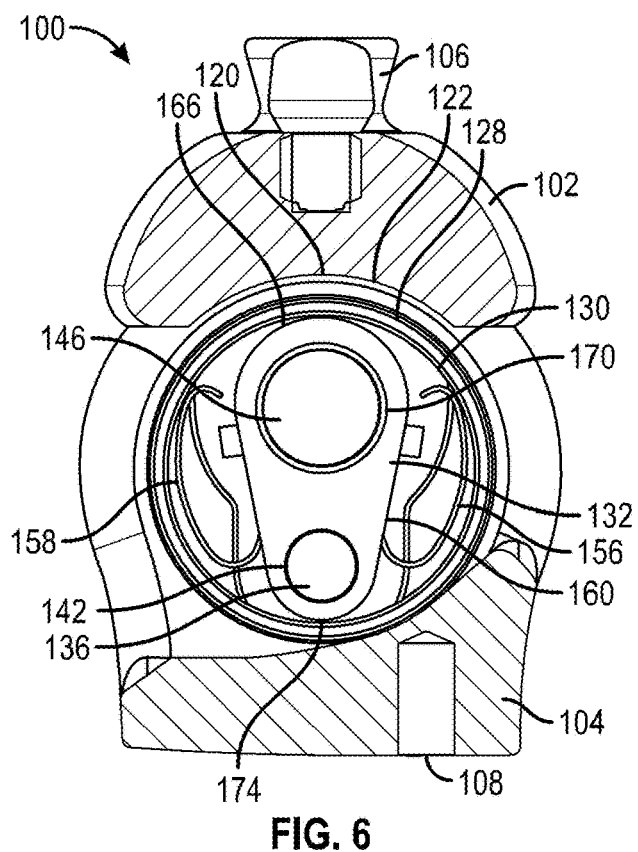
FIG. 6 is a cross-sectional side view of the prosthetic joint of FIG. 1 in the unlocked configuration.
Figure 7:
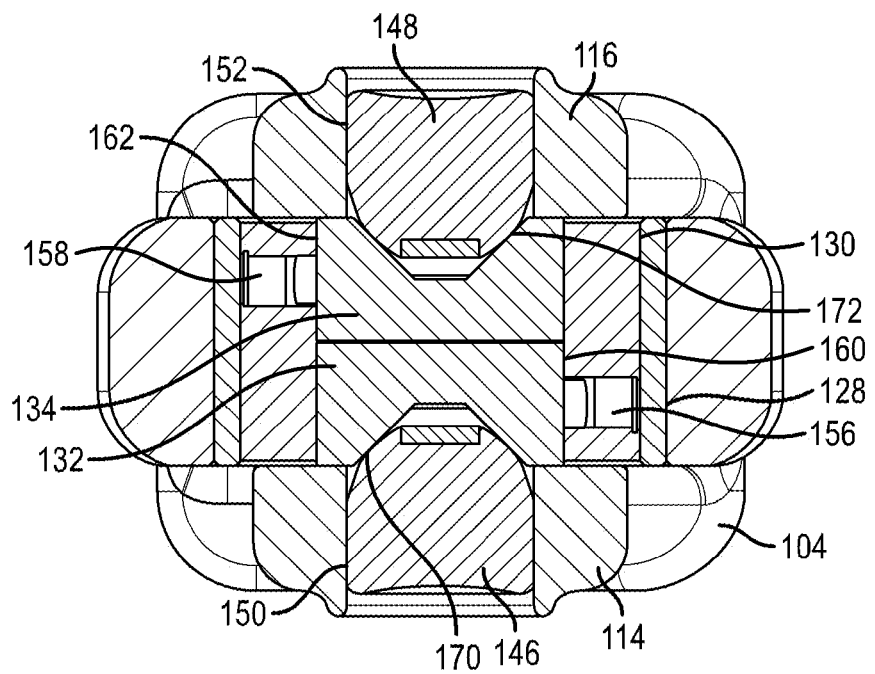
FIG. 7 is a cross-sectional top view of the prosthetic joint of FIG. 1 in the unlocked configuration.
Figure 8:
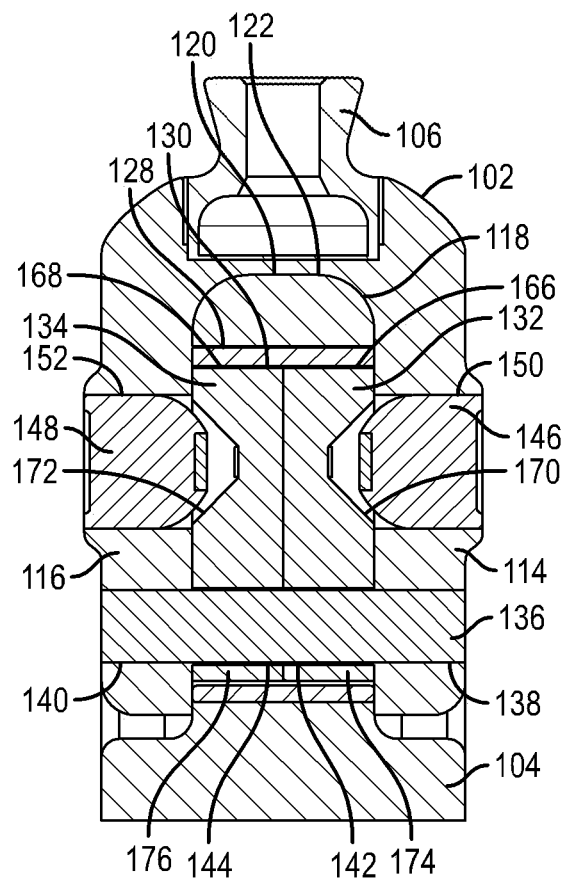
FIG. 8 is a transverse cross-sectional view of the prosthetic joint of FIG. 1 in the unlocked configuration.

FIGS. 6-8 show the prosthetic joint 100 in the unlocked configuration. The first cam 132 can be aligned along the diameter of the cylindrical chamber 128. The longitudinal dimension of the first cam 132 can be less than the diameter of the cylindrical chamber 128. In the unlocked configuration, the proximal portion 166 of the first cam 132 may not make contact with, abut, or otherwise touch the cylindrical track 130 of the cylindrical chamber 128. The second cam 134 can be aligned along the diameter of the cylindrical chamber 128. The longitudinal dimension of the second cam 134 can be less than the diameter of the cylindrical chamber 128. In the unlocked configuration, the proximal portion 168 of the second cam 134 may not make contact with, abut, or otherwise touch the cylindrical track 130 of the cylindrical chamber 128.

The biasing force of the first cam spring 156 can be overcome. The first cam 132 can be moved in the second direction, into alignment with the second cam 134. The biasing force of the second cam spring 158 can be overcome. The second cam 134 can be moved in the first direction, into of alignment with the first cam 132.

FIGS. 6-8 shows the prosthetic joint 100 in the unlocked configuration. To unlock the prosthetic joint 100, the first positioning member 146 is pushed or otherwise depressed inward (e.g., manually depressed), toward the first cam 132. The second positioning member 148 is pushed or otherwise depressed inward (e.g., manually depressed), toward the second cam 134. The first positioning member 146 is slid within the first positioning hole 150 of the first distally extending arm 114. The second positioning member 148 is slid within the second positioning hole 152 of the second distally extending arm 116. The first positioning member 146 can be slid first, the second positioning member 148 can be slid first, or the first positioning member 146 and the second positioning member 148 can be slid simultaneously.

The tip of the first positioning member 146 slides against the detent 170 of the first cam 132. The tip of the second positioning member 148 slides against the detent 172 of the second cam 134. The positioning members 146, 148 are pressed inward until the positioning members 146, 148 overcome the biasing force of the first cam spring 156 and the second cam spring 158. Further motion of the first positioning member 146 and the second positioning member 148 inward causes the first cam 132 to align with the second cam 134. As shown in FIG. 7, the first positioning member 146 can be concentric, generally concentric or more concentric than in the locked configuration with respect to the first detent 170. The second positioning member 148 can be concentric, generally concentric or more concentric than in the locked configuration with respect to the second detent 172.

The first positioning member 146 can overcome the biasing force of the first cam spring 156 and the second positioning member 148 can overcome the biasing force of the second cam spring 158. The first positioning member 146 can move the first cam 132 in the second direction, toward alignment with the second cam 134. The second positioning member 148 can move the second cam 134 in the first direction, toward alignment with the first cam 132. In some embodiments, the proximal portion 166 of the first cam 132 is not in contact with the cylindrical track 130 in the unlocked configuration. In some embodiments, the proximal portion 168 of the second cam 134 is in contact with the cylindrical track 130 in the unlocked configuration.

In the unlocked configuration, the first attachment member 102 is permitted to rotate with respect to the second attachment member 104. The first positioning member 146 overcomes the biasing force of the first cam spring 156. The second positioning member 148 overcomes the biasing force of the second cam spring 158. In this configuration, the first cam 132, the second cam 134, the first cam spring 156, and the second cam spring 158 do not resist rotational movement. The first attachment member 102 and the second attachment member 104 can rotate with respect to each other. The first distally extending arm 114, the second distally extending arm 116, the first cam 132, the second cam 134, the axle 136, the first positioning member 146, and the second positioning member 148 can rotate as a unit with respect to the second attachment member 104.

In some embodiments, in the unlocked configuration, the first cam 132 can have zero points of contact with the cylindrical track 130 of the cylindrical chamber 128. In some embodiments, the second cam 134 can have zero points of contact with the cylindrical track 130 of the cylindrical chamber 128 in the unlocked configuration. In some embodiments, in the unlocked configuration, the first cam 132 can have one point of contact with the cylindrical track 130 of the cylindrical chamber 128. In some embodiments, the distal portion 174 of the first cam 132 and the distal portion 176 of the second cam 134 each have a point of contact in the unlocked configuration.

In the unlocked configuration, the first cam 132 and the second cam 134 can be rotated within the cylindrical track 130 of the cylindrical chamber 128. In the unlocked configuration, the first attachment member 102 can be rotated to different orientations with respect to the second attachment member 104. After the desired orientation is reached, the first positioning member 146 and the second positioning member 148 can be released. The first cam 132 can then be biased by the first cam spring 156 against the cylindrical track 130. The second cam 134 can then be biased by the second cam spring 158 against the cylindrical track 130. In some embodiments, the positioning members 146, 148 are released simultaneously. When the positioning members 146, 148 are released, the prosthetic joint 100 reverts or otherwise transitions to the locked configuration.

In the unlocked configuration, the center of rotation of the cams 132, 134 coincides with the center of rotation of the cylindrical chamber 128. The cams 132, 134 are held by the positioning members 146, 148 in alignment with the distally extending arms 114, 116. The cams 132, 134 can rotate about the midpoint of the cylindrical chamber 128. In the locked configuration, the cams 132, 134 are not held in alignment. Rather, the first cam spring 156 pushes the first cam 132 in a first direction and the second cam spring 158 pushes the second cam 134 in a second direction (see FIG. 4). The center of rotation of the cams 132, 134 no longer coincides with the center of rotation of the cylindrical chamber 128 in the locked configuration.

In the unlocked configuration, the user can rotate the first attachment member 102 with respect to the second attachment member 104. In the unlocked configuration, the user can rotate the second attachment member 104 with respect to the first attachment member 102. In some embodiments, the user depresses the first positioning member 146 and the second positioning member 148 during rotation of the first attachment member 102 and the second attachment member 104.

Upon reaching the desired angular orientation of the first attachment member 102 with respect to the second attachment member 104, the user can release the first positioning member 146 and the second positioning member 148. The first positioning member 146 can be released first, the second positioning member 148 can be released first, or the first positioning member 146 and the second positioning member 148 can be released simultaneously.

Upon release of the first positioning member 146, the first cam spring 156 biases the first cam 132 in the first direction, out of alignment with the second cam 134. The first detent 170 can interact with the first positioning member 146 such that the first positioning member 146 slides within the first positioning hole 150 away from the first cam 132. For instance, the first detent 170 can be tapered and the first positioning member 146 can be tapered. The tapered wall of the first detent 170 can exert a force on the tapered tip of the first positioning member 146. The tapered tip of the first positioning member 146 can become more eccentric as the first positioning member 146 slides within the first positioning hole 150.

Upon release of the second positioning member 148, the second cam spring 158 biases the second cam 134 in the second direction, out of alignment with the first cam 132. The second detent 172 can interact with the second positioning member 148 such that the second positioning member 148 slides within the second positioning hole 152 away from the second cam 134. For instance, the second detent 172 can be tapered and the second positioning member 148 can be tapered. The tapered wall of the second detent 172 can exert a force on the tapered tip of the second positioning member 148. The tapered tip of the second positioning member 148 can become more eccentric as the second positioning member 148 slides within the second positioning hole 152.

Upon release of the positioning members 146, 148, the first cam spring 156 biases the proximal portion 166 of the first cam 132 against the cylindrical track 130. The second cam spring 158 similarly biases the proximal portion 168 of the second cam 134 against the cylindrical track 130. The first cam spring 156 and the second cam spring 158 bias the cams 132, 134 out of alignment with each other, as shown in FIGS. 3 and 4. In the locked configuration, the first attachment member 102 is inhibited (e.g., prevented) from rotating with respect to the second attachment member 104. As shown in FIG. 3, the first cam 132 is biased by the first cam spring 156 in a first direction against the cylindrical track 130 and the second cam 134 is biased by the second cam spring 158 in a second direction (e.g., an opposite direction to the first direction) against the cylindrical track 130. In embodiments that use only the first cam spring 156 to bias the first cam 132, the single cam spring 156 biases the first cam 132 relative to the second cam 134 to inhibit (e.g., prevent) the first attachment member 102 from rotating relative to the second attachment member 104.

FIGS. 9-14 depict another embodiment of a prosthetic joint 200. The prosthetic joint 200 can have similar features to those described with respect to prosthetic joint 100. Similar components can include similar reference numerals. The prosthetic joint 200 can include a first attachment member 202 and a second attachment member 204. The prosthetic joint 200 can attach to a user or to another prosthetic device with the first attachment member 202. The prosthetic joint 200 can attach to a user or to another prosthetic device with the second attachment member 204. The first attachment member 202 is depicted as including a first connection portion 206 shown in the illustrated embodiment as a pyramid connector. The first connection portion 206 can attach to a socket that receives a stump of a user, to another prosthetic device (e.g., a pylon), or to any other appropriate object. Further, it will be understood that the first connection portion 206 can in other embodiments include attachment features other than a pyramid connector, such as a hole and pin, a threaded hole or screw, a latch, a magnetic member, tube clamp, or other features. In some embodiments, the second attachment member 204 includes a second connection portion 208. The second connection portion 208 can include a pyramid connector, a hole and pin, a threaded hole or screw, a latch, a magnetic member, tube clamp, or other features.

In some embodiments, the first attachment member 202 can include a first distally extending lid 278 and a second distally extending lid 280. In some embodiments, the first distally extending lid 278 can be identical, substantially similar or a mirror image of the second distally extending lid 280. The first distally extending lid 278 and the second distally extending lid 280 can be positioned on opposite sides of the first attachment member 202.

In between the distally extending lids 278, 280, the first attachment member 202 can have a space 218 sized to accept the second attachment member 204. The space 218 can permit the first attachment member 202 and the second attachment member 204 to rotate relative to each other. The space 218 can be defined by an inner surface of the first distally extending lid 278, an inner surface of the second distally extending lid 280, and an inner surface 220. The inner surface 220 can be curved or concave. In some embodiments, the second attachment member 204 can include a curved or convex outer surface 222. The inner surface 220 of the first attachment member 202 can provide a bearing surface for the outer surface 222 of the second attachment member 204. The inner surface 220 of the first attachment member 202 can permit the outer surface 222 of the second attachment member 204 to rotate thereon. In other embodiments, the inner surface 220 of the first attachment member 202 does not contact the outer surface 222 of the second attachment member 204.

Figure 9:
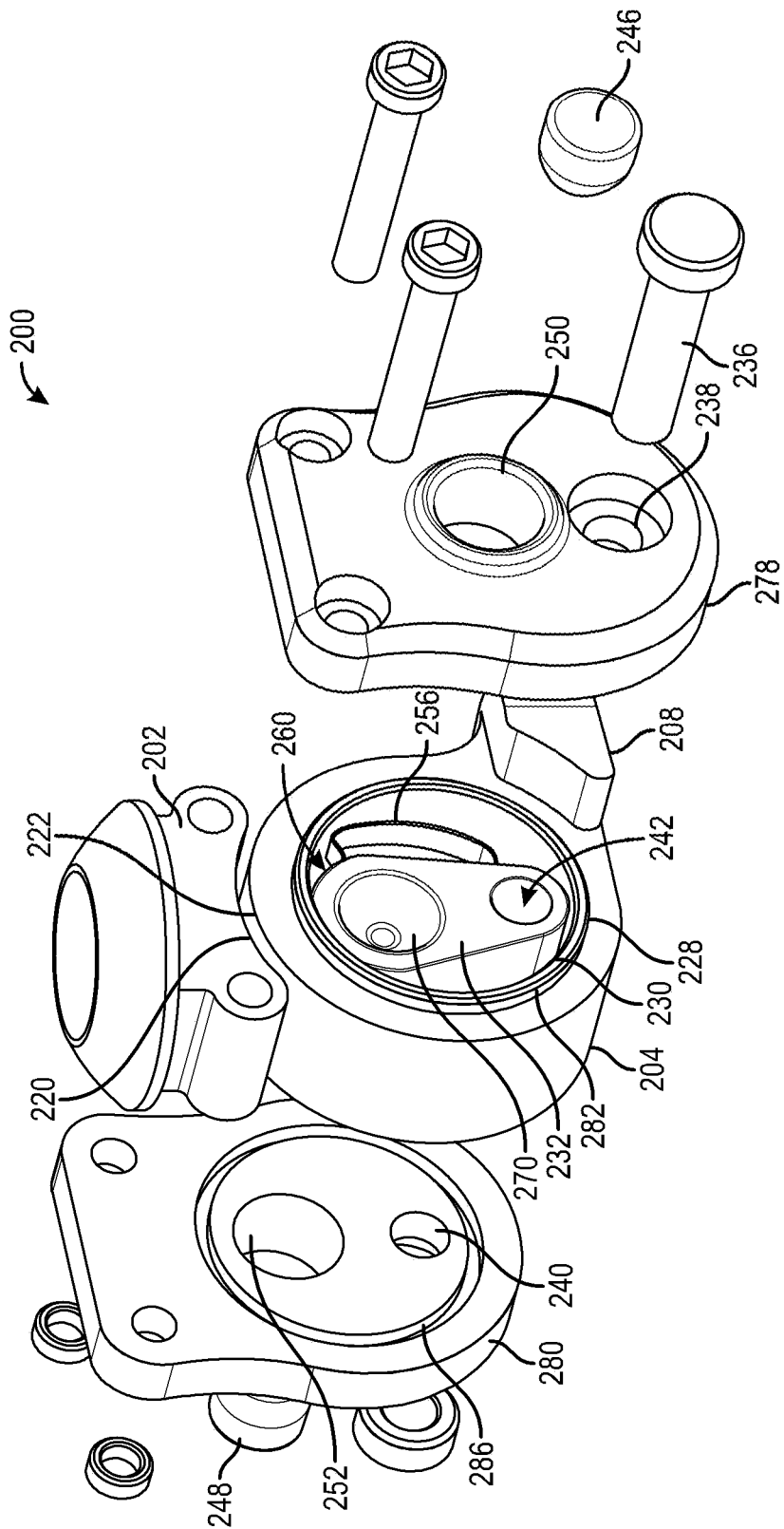
FIG. 9 is a perspective exploded view of an embodiment of a prosthetic joint.
Figure 10:
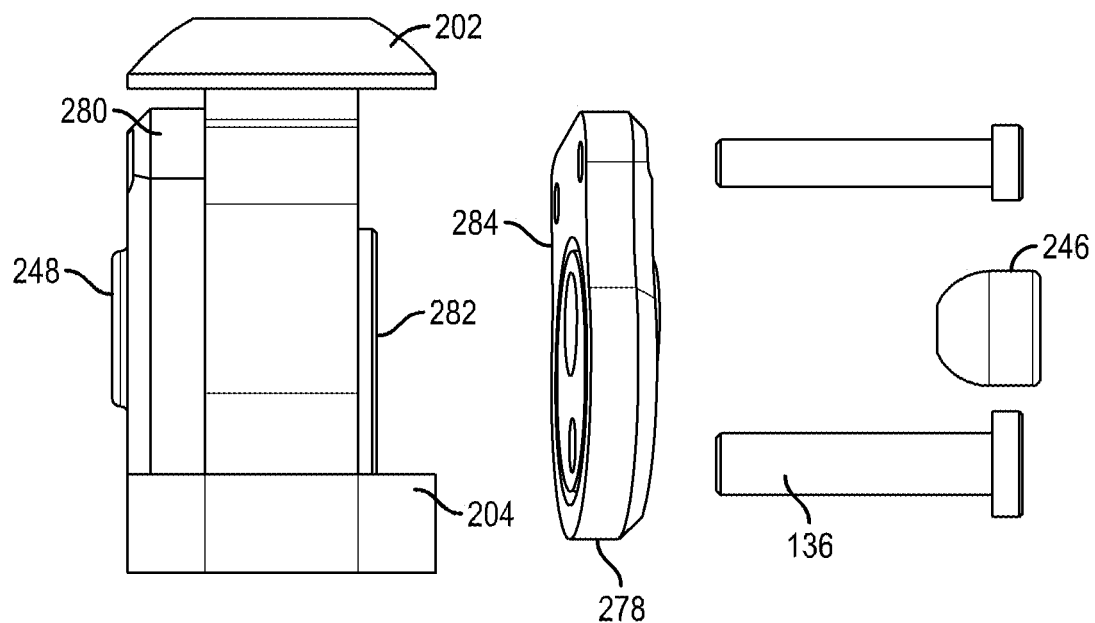
FIG. 10 is a partially assembled front view of the prosthetic joint of FIG. 9.
Figure 11:
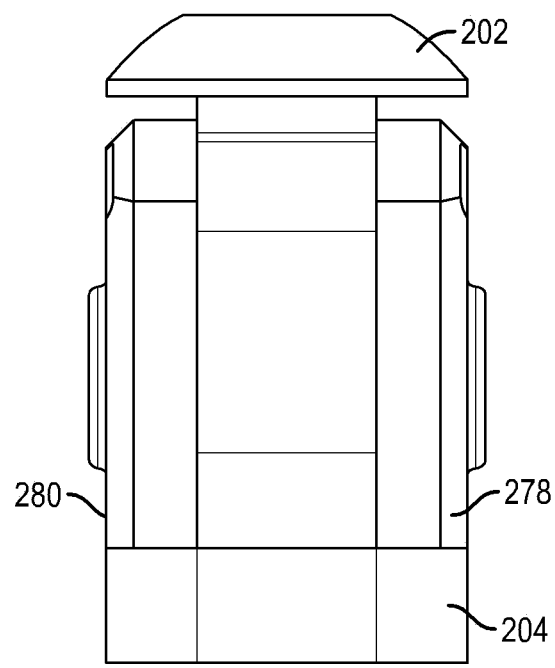
FIG. 11 is a fully assembled front view of the prosthetic joint of FIG. 9.
Figure 12:
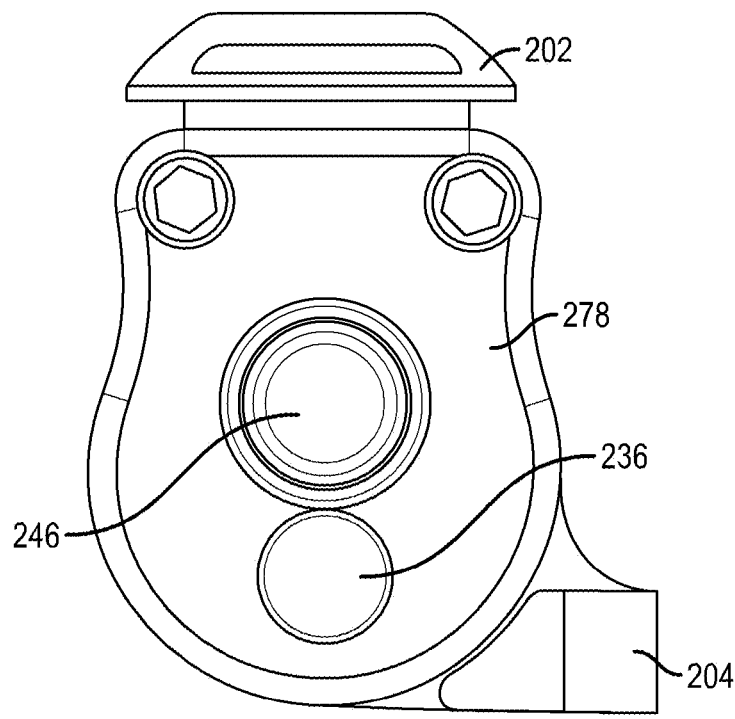
FIG. 12 is a fully assembled side view of the prosthetic joint of FIG. 9.

As shown in FIG. 9, the second attachment member 204 can include a cylindrical chamber 228. The cylindrical chamber 228 can define a cylindrical track 230. The prosthetic joint 200 can include one or more cams. In the illustrated embodiment, the cams include a first cam 232 and a second cam 234. The cylindrical chamber 228 can include a chamber lip 282. The chamber lip 282 can extend from the second attachment member 204. The chamber lip 282 can extend into the first distally extending lid 278, the second distally extending lid 280 or both the first distally extending lid 278 and the second distally extending lid 280. The first distally extending lid 278 can include a complementary first groove 284 sized to accept the chamber lip 282. The second distally extending lid 280 can include a complementary second groove 286 sized to accept the chamber lip 282. The first groove 284 of the first distally extending lid 278 can provide a bearing surface for the chamber lip 282. The second groove 286 of the second distally extending lid 280 can provide a bearing surface for the chamber lip 282. The chamber lip 282 and the grooves 284, 286 can provide a more robust connection between the first attachment member 202 and the second attachment member 204.

The cylindrical lip 282 can extend past a face of the second attachment member 204. The chamber lip 282 can extend past two faces of the second attachment member 204. When the prosthetic joint 200 is assembled, the chamber lip 282 on the second attachment member 204 can abut or otherwise fit within the groove 284 of the first distally extending lid 278. When the prosthetic joint 200 is assembled, the chamber lip 282 can abut or otherwise fits within the groove 286 of the second distally extending lid 278. The inner surface of the first distally extending lid 278 can fit within the cylindrical chamber 228. The inner surface of the second distally extending lid 280 can fit within the cylindrical chamber 228.

The first cam 232 and the second cam 234 are sized to fit within the cylindrical chamber 228 of the second attachment member 204. For instance, the first cam 232 and the second cam 234 together can have a smaller width than the cylindrical chamber 228. The first cam 232 and the second cam 234 can be sized to fit within the cylindrical chamber 228 less the chamber lip 282. For instance, the first cam 232 and the second cam 234 together can have a smaller width than the cylindrical chamber 228 less the chamber lip 282. The first cam 232 and the second cam 234 can be sized to fit within the second attachment member 204. For instance, the first cam 232 and the second cam 234 together can have a smaller width than second attachment member 204.

The first distally extending lid 278 can be coupled to the first attachment member 202. The second distally extending lid 280 can be coupled to the first attachment member 202. In the illustrated embodiment, a pair of fasteners passes through the first distally extending lid 278, the first attachment member 202, and second distally extending lid 280. For instance, the heads of the fasteners can be near the first distally extending lid 278 and the nuts of the fasteners can be near the second distally extending lid 280. Other methods of fastening the first distally extending lid 278, the first attachment member 202, and second distally extending lid 280 are contemplated.

The first attachment member 202 can provide a rotatable connection with the second attachment member 204. The first attachment member 202 can include an axle 236. The axle 236 can pass through the first distally extending lid 278 and the second distally extending lid 280. In some embodiments, the axle 236 passes through a first hole 238 in the first distally extending lid 278. In some embodiments, the axle 236 passes through a second hole 240 in the second distally extending lid 280. The first hole 238 can be near a distal end of the first distally extending lid 278 and the second hole 240 can be near a distal end of the second distally extending lid 280.

In some embodiments, the first cam 232 can include or define a first cam hole 242 and the second cam 234 can include or define a second cam hole 244. The axle 236 can extend through the first cam hole 242 and the second cam hole 244, as described above with respect to prosthetic joint 100. In the illustrated embodiment, the axle 236 passes through a first hole 238 in the first distally extending lid 278, the first cam hole 242 in the first cam 232, the second cam hole 244 in the second cam 234, and the second hole 240 in the second distally extending lid 280 respectively. The first attachment member 202, first distally extending lid 278, the second distally extending lid 280, and the axle 236 can be rigidly coupled.

The prosthetic joint 200 can include one or more unlocking members. In the illustrated embodiment, the unlocking member includes a first positioning member 246 and a second positioning member 248. The first distally extending lid 278 can be associated with a first positioning member 246. The first positioning member 246 can extend through a first positioning hole 250 in the first distally extending lid 278. The first positioning member 246 can make contact with, abut, or otherwise touch the first cam 232. The first positioning member 246 can be retained within the first positioning hole 250 to permit movement along the width of the prosthetic joint 200. The second distally extending lid 280 can be associated with a second positioning member 248. The second positioning member 248 can extend through a second positioning hole 252 in the second distally extending lid 280. The second positioning member 246 can make contact with, abut, or otherwise touch the second cam 234. The second positioning member 248 can be retained within the second positioning hole 252 to permit movement along the width of the prosthetic joint 200.

The prosthetic joint 200 can include one or more biasing member. In the illustrated embodiment, the biasing member includes a first cam spring 256 and a second cam spring 258. The first end of the first cam spring 256 can be coupled to the first cam 232. The first cam spring 256 biases the first cam 232 in a first direction. The first end of the second cam spring 258 can be coupled to the second cam 234. The second cam spring 258 biases the second cam 234 in a second direction different than the first direction. In a locked configuration, the first cam spring 256 and the second cam spring 258 bias the cams 232, 234 out of alignment with each other, as described above with respect to prosthetic joint 100.

FIGS. 9-12 show the prosthetic joint 200 in the locked configuration. In the locked configuration, the first cam spring 256 and the second cam spring 258 bias the cams 232, 234 out of alignment with each other. The first cam 232 is offset with respect to the second cam 234 in a locked configuration. The first positioning member 246 can be eccentric with respect to a first detent 270 of the first cam 232. The second positioning member 248 can be similarly eccentric with respect to a second detent 272 of the second cam 234. The proximal portion 266 of the first cam 232 is in contact with the cylindrical track 230. The proximal portion 268 of the second cam 234 is in contact with the cylindrical track 230.

Figure 13:
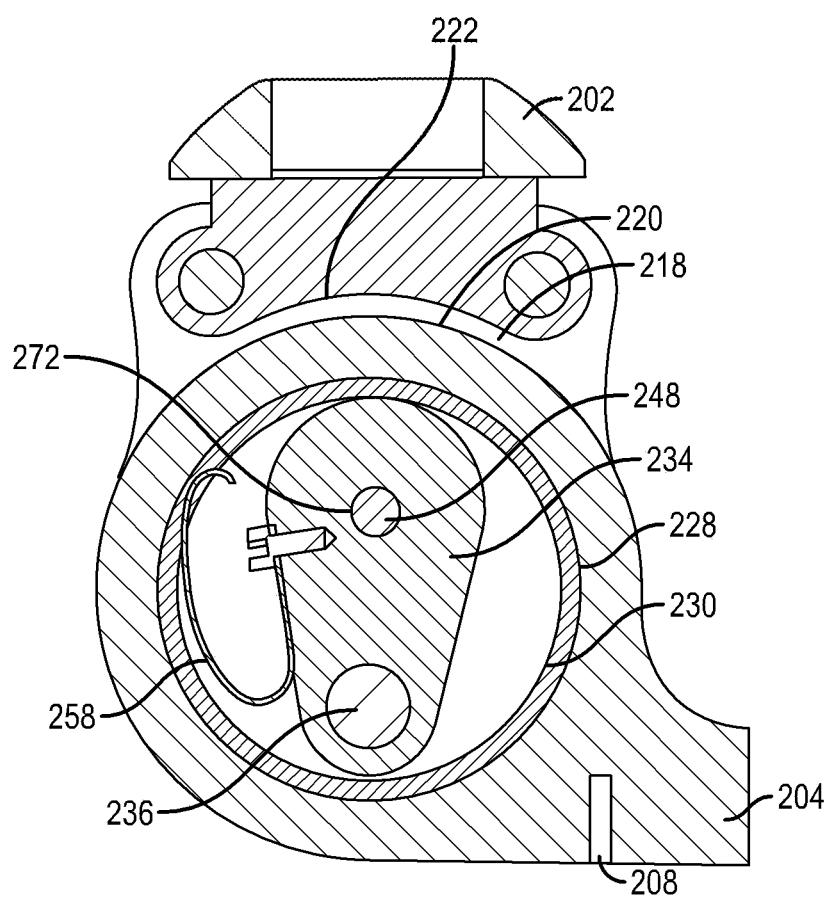
FIG. 13 is a cross-sectional side view of the prosthetic joint of FIG. 9 in the unlocked configuration.
Figure 14:
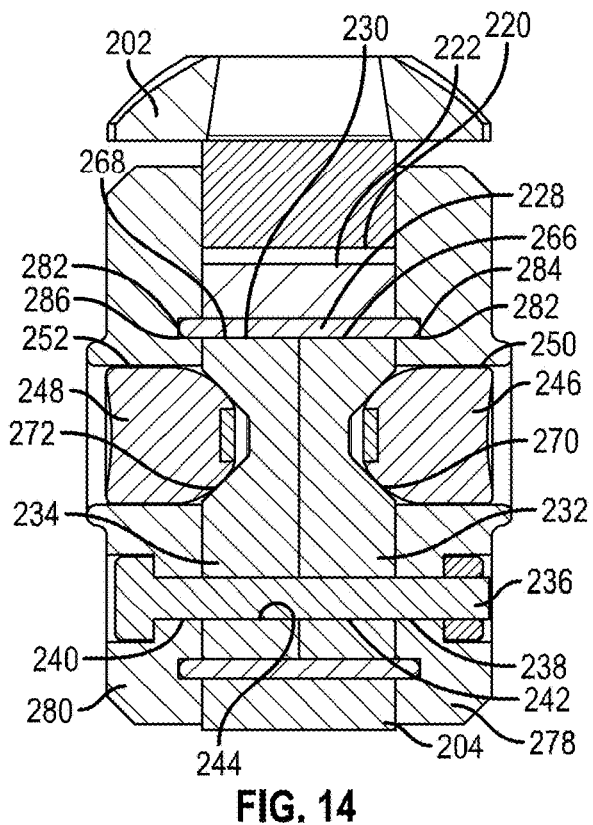
FIG. 14 is a transverse cross-sectional view of the prosthetic joint of FIG. 9 in the unlocked configuration.
Figure 15:
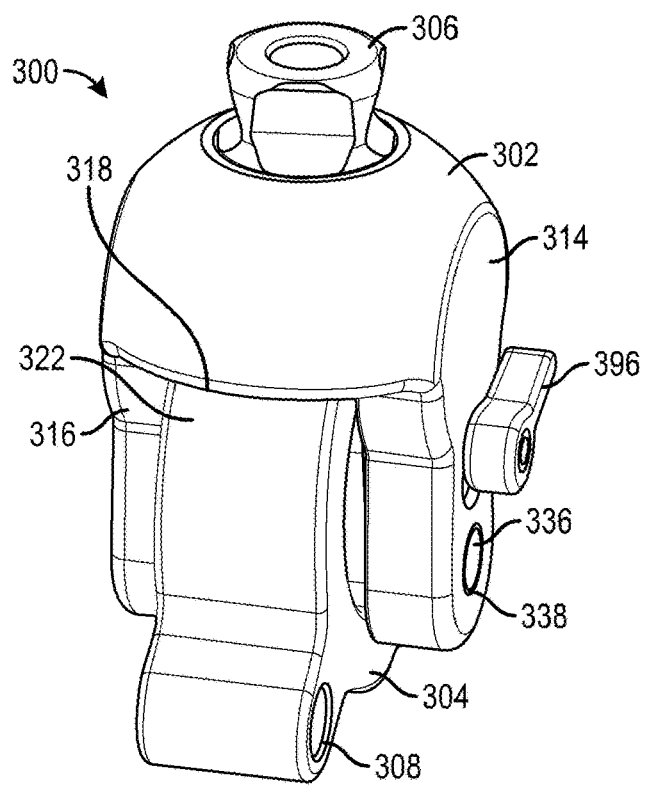
FIG. 15 is a perspective view of an embodiment of a prosthetic joint.
Figure 16:
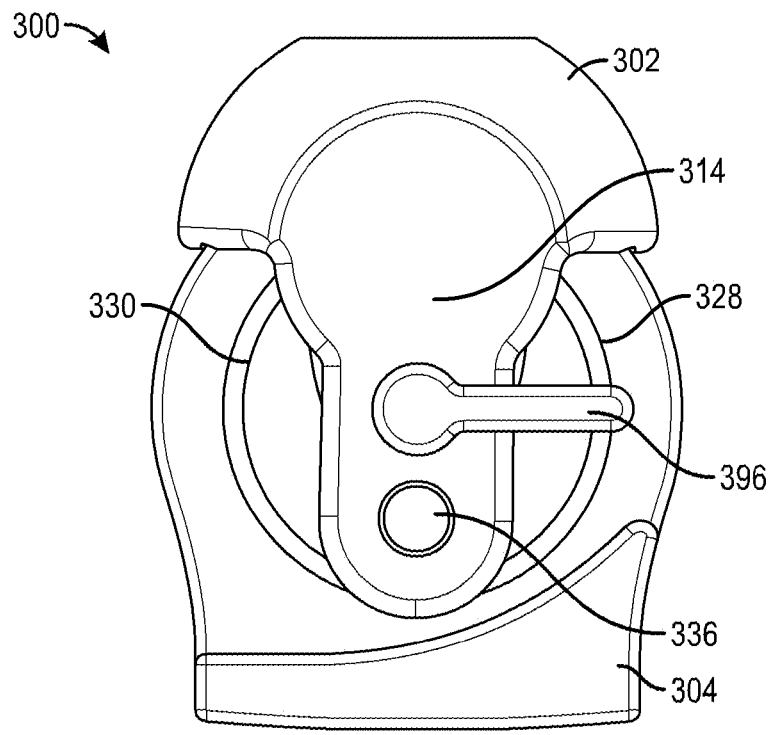
FIG. 16 is a side view of the prosthetic joint of FIG. 15 in the locked configuration.

FIGS. 13-14 show the prosthetic joint 200 in the unlocked configuration, similar to the unlocked configuration described above with respect to prosthetic joint 100. To unlock the prosthetic joint 200, the first positioning member 246 is pushed or otherwise depressed inward (e.g., manually depressed), toward the first cam 232. The second positioning member 248 is pushed or otherwise depressed inward (e.g., manually depressed), toward the second cam 234. The first positioning member 246 is slid within the first positioning hole 250 of the first distally extending lid 278. The second positioning member 248 is slid within the second positioning hole 252 of the second distally extending lid 280. The biasing force of the first cam spring 256 can be overcome. The first cam 232 can move in the second direction, into alignment with the second cam 234. In the unlocked configuration, the proximal portion 266 of the first cam 232 does not make contact with, abut, or otherwise touch the cylindrical track 230 of the cylindrical chamber 228. The biasing force of the second cam spring 258 can be overcome. The second cam 234 can move in the first direction, into of alignment with the first cam 232. In the unlocked configuration, the proximal portion 268 of the second cam 234 does not make contact with, abut, or otherwise touch the cylindrical track 230 of the cylindrical chamber 228.

In the unlocked configuration, the first attachment member 202 is permitted to rotate with respect to the second attachment member 204. The first attachment member 202, the first distally extending lid 278, the second distally extending lid 280, the first cam 232, the second cam 234, the axle 236, the first positioning member 246, and the second positioning member 248 can rotate as a unit with respect to the second attachment member 204.

Upon reaching the desired angular orientation of the first attachment member 202 with respect to the second attachment member 204, the first positioning member 246 and the second positioning member 248 can be released (e.g., manually released). Upon release of the first positioning member 246, the first cam spring 256 biases the first cam 232 in the first direction, out of alignment with the second cam 234. Upon release of the second positioning member 248, the second cam spring 258 biases the second cam 234 in the first direction, out of alignment with the first cam 232. Upon release of the positioning members 246, 248, the first cam spring 256 biases the proximal portion 266 of the first cam 232 against the cylindrical track 230. The second cam spring 258 similarly biases the proximal portion 268 of the second cam 234 against the cylindrical track 230.

FIGS. 15-23 depict an embodiment of a prosthetic joint 300. The prosthetic joint 300 can have similar features to those described with respect to prosthetic joint 100 or 200. Similar components can include similar reference numerals. The prosthetic joint 300 can include a first attachment member 302 and a second attachment member 304. In some embodiments, the first attachment member 302 can include a first distally extending arm 314 and a second distally extending arm 316. In some embodiments, the first distally extending arm 314 can be identical, substantially similar or a mirror image of the second distally extending arm 316. In some embodiments, the first distally extending arm 314 can have more or less features, such as holes, as the second distally extending arm 316. The second attachment member 304 can include a cylindrical chamber 328. The cylindrical chamber 228 can define a cylindrical track 330.

The first attachment member 302 can provide a rotatable connection with the second attachment member 304. The first attachment member 302 can include an axle 336. The axle 336 can pass through the first distally extending arm 314 and the second distally extending arm 316. In some embodiments, the axle 336 passes through a first hole 338 in the first distally extending arm 314 and a second hole 340 in the second distally extending arm 316.

The prosthetic joint 300 can include a first cam 332 and a second cam 334. In some embodiments, the first cam 332 can include or define a first cam hole 342 and the second cam 334 can include or define a second cam hole 344. The axle 336 can extend through the first cam hole 342 and the second cam hole 344. In the illustrated embodiment, the axle 336 passes through a first hole 338 in the first distally extending arm 314, the first cam hole 342 in the first cam 332, the second cam hole 344 in the second cam 334, and the second hole 340 in the second distally extending arm 316 respectively. The first distally extending arm 314, the second distally extending arm 316, and the axle 336 can be rigidly coupled. When the prosthetic joint 300 is assembled, the first attachment member 302 is coupled to the second attachment member 304 via the first cam 332 and the second cam 334.

Figure 18:
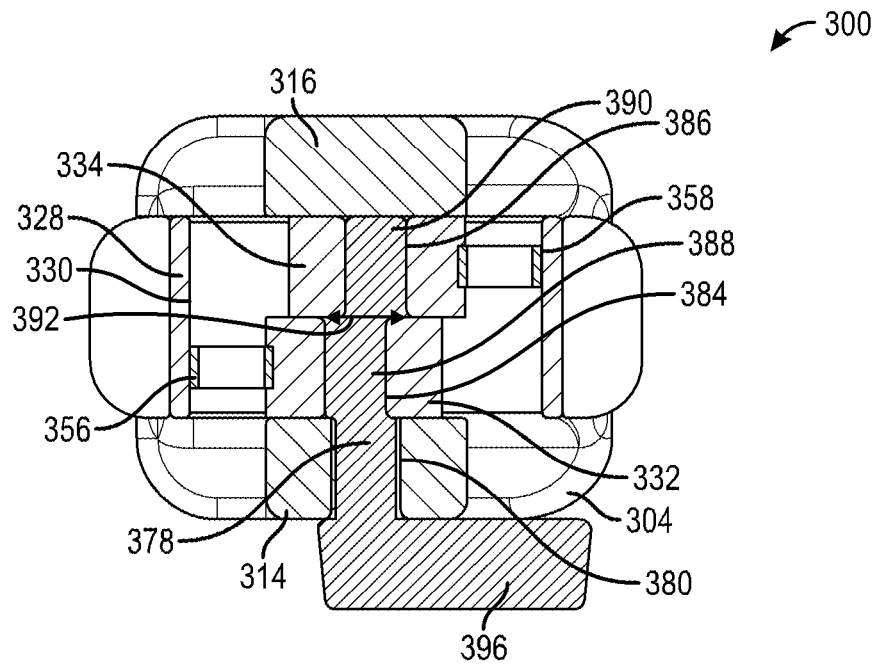
FIG. 18 is a cross-sectional top view of the prosthetic joint of FIG. 15 in the locked configuration.

The prosthetic joint 300 can include one or more unlocking members. In the illustrated embodiment, the unlocking member includes a turnkey 378. The turnkey 378 can be an elongate shaft, as described herein. The turnkey 378 can be coupled to a handle 396. The handle 396 can be configured to rotate the turnkey 378 within the prosthetic joint 300. As shown in FIG. 18, the turnkey 378 can pass through the first distally extending arm 314. In some embodiments, the turnkey 378 passes through a first turnkey hole 380 in the first distally extending arm 314. In some embodiments, such as the illustrated embodiment, the turnkey 378 passes only through one of the first and second distally extending arms 314, 316. In other embodiments not shown, the turnkey 378 can pass through the first distally extending arm 314 and the second distally extending arm 316. In other embodiments not shown, the turnkey 378 passes through a first turnkey hole 380 in the first distally extending arm 314 and a second turnkey hole (not shown) in the second distally extending arm 316.

In some embodiments, the first cam 332 can include or define a first turnkey cam hole 384 and the second cam 334 can include or define a second turnkey cam hole 386. The turnkey 378 can extend through the first turnkey cam hole 384 and the second turnkey cam hole 386. In the illustrated embodiment, the turnkey 378 passes through a first turnkey hole 380 in the first distally extending arm 314, the first turnkey cam hole 384 in the first cam 332, and the second turnkey cam hole 386 in the second cam 334 respectively. The first distally extending arm 314, the second distally extending arm 316, the axle 336 and the turnkey 378 can be rigidly coupled.

Figure 19:
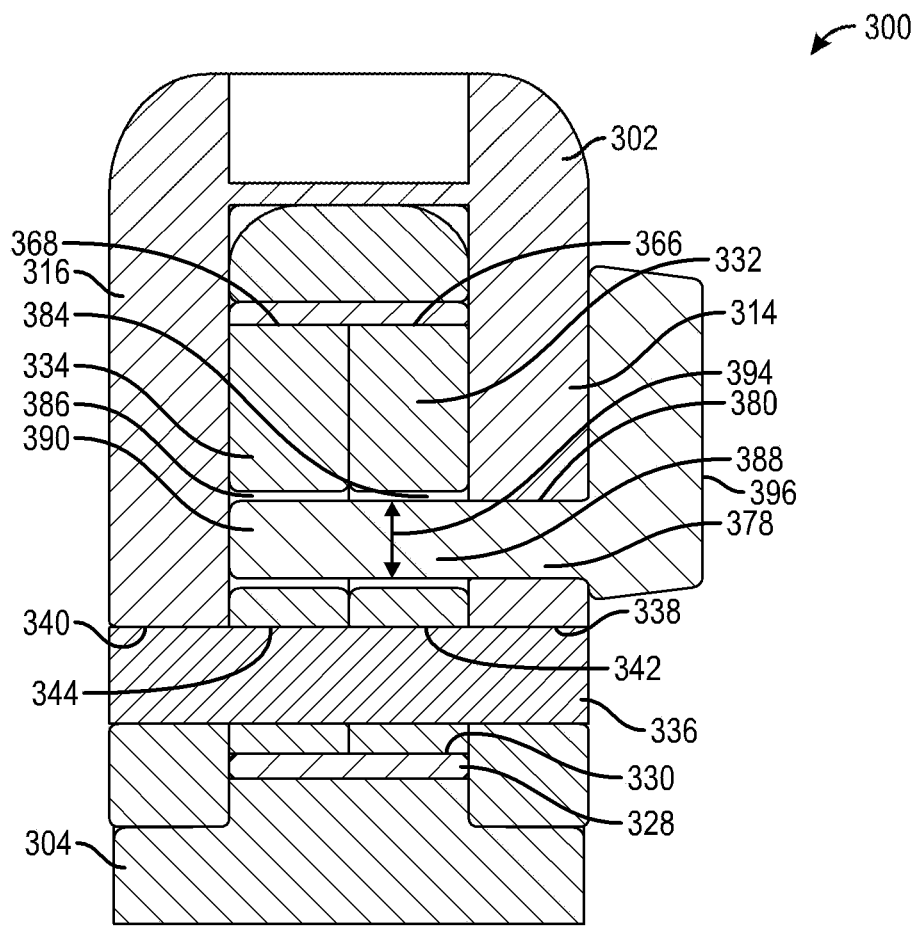
FIG. 19 is a transverse cross-sectional view of the prosthetic joint of FIG. 15 in the locked configuration.
Figure 20:
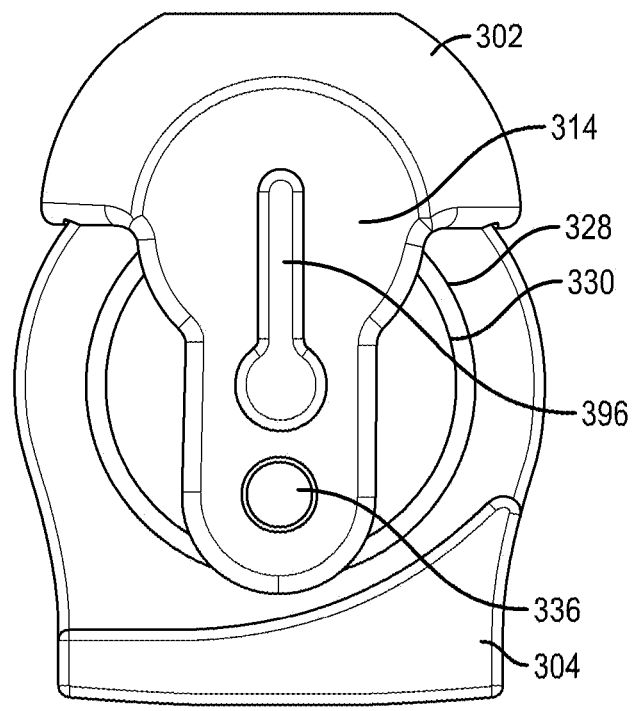
FIG. 20 is a side view of an embodiment of the prosthetic joint of FIG. 15 in the unlocked configuration.
Figure 21:
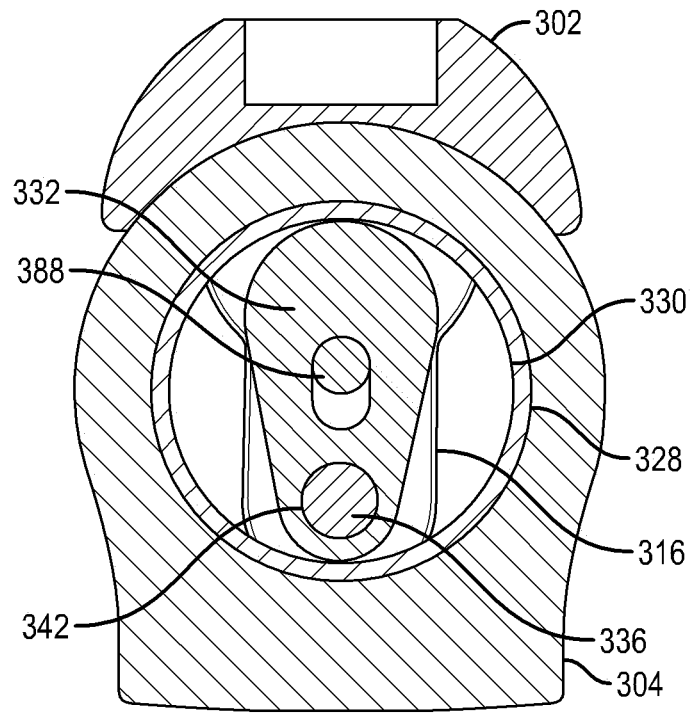
FIG. 21 is a cross-sectional side view of the prosthetic joint of FIG. 15 in the unlocked configuration.
Figure 22:
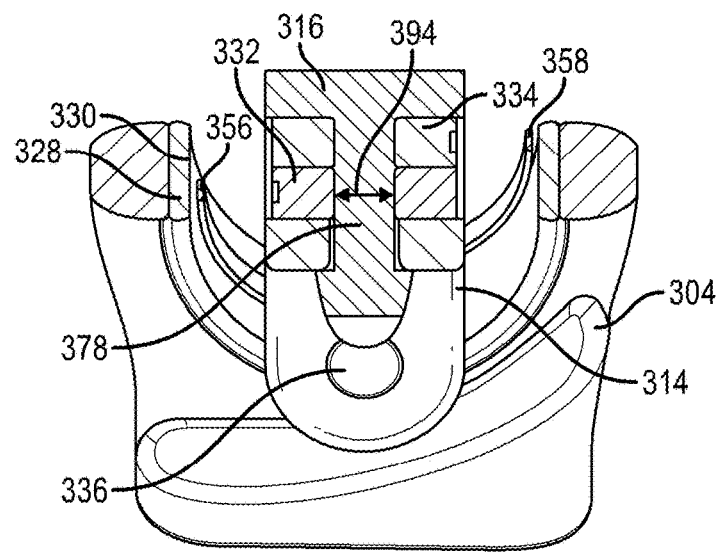
FIG. 22 is a cross-sectional top view of the prosthetic joint of FIG. 15 in the unlocked configuration.
Figure 23:
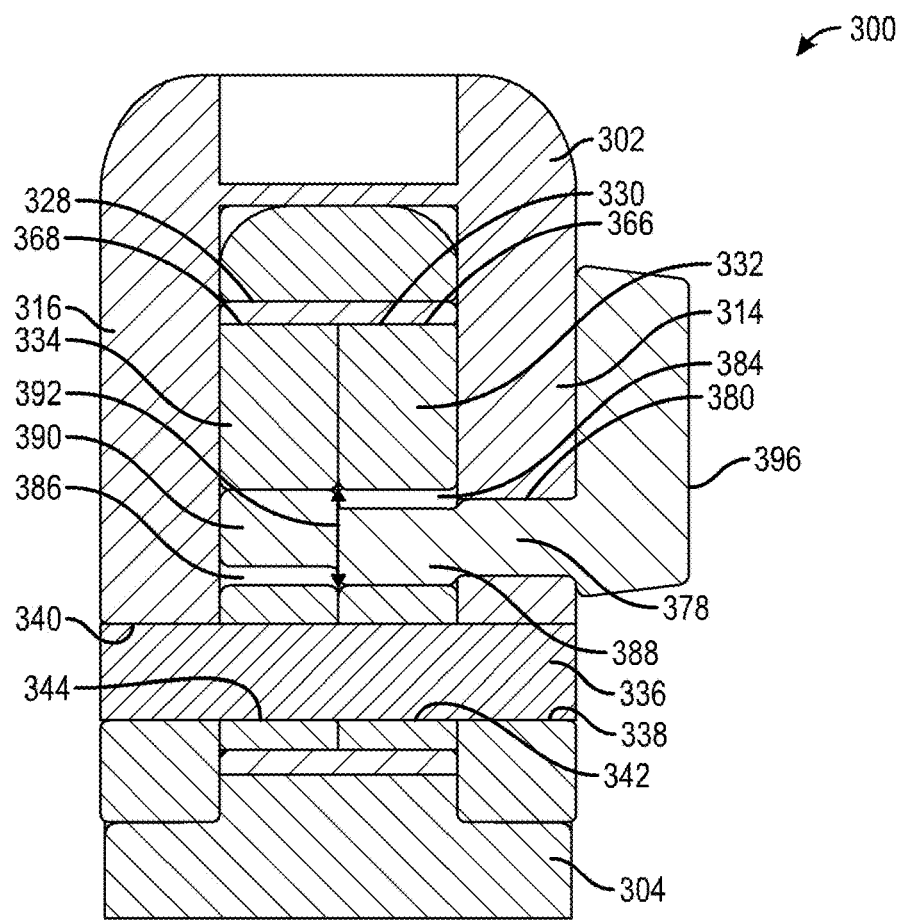
FIG. 23 is a transverse cross-sectional view of the prosthetic joint of FIG. 15 in the unlocked configuration.

The turnkey 378 has a first pin portion 388 disposed within the first turnkey cam hole 384 of the first cam 332. The turnkey 378 has a second pin portion 390 disposed within the second turnkey cam hole 386 of the second cam 334. As shown in FIG. 18, the first pin portion 388 and the second pin portion 390 have a width along the width of the prosthetic joint 300, a first dimension 392 and a second dimension 394. As shown in FIGS. 18 and 23, the turnkey 378 can have a non-constant, non-uniform first dimension 392 measured in a first plane along a length of the turnkey 378. The first dimension 392 can be along an axis that is perpendicular to the width of the prosthetic joint 300. As shown in FIGS. 19 and 22, the turnkey 300 can have a constant, uniform second dimension 394 measured in a second plane perpendicular to the first plane along a length of the turnkey 378. The second dimension 394 can be along an axis that is perpendicular to the width of the prosthetic joint 300. When the first dimension 392 is in contact with the first cam 332 and the second cam 334, the cams 332, 334 are offset (e.g., not aligned) relative to each other and the prosthetic joint 300 is in the locked configuration. When the second dimension 394 is in contact with the first cam 332 and the second cam 334, the cams 332, 334 are aligned with each other and the prosthetic joint 300 is in the unlocked configuration.

The prosthetic joint 300 can include one or more biasing members. In the illustrated embodiment, the biasing member includes a first cam spring 356 and a second cam spring 358, as shown in FIGS. 18 and 22. The first end of the first cam spring 356 can be coupled to the first cam 332. The first end of the second cam spring 358 can be coupled to the second cam 334. The first cam spring 356 biases the first cam 332 in a first direction. The second cam spring 358 biases the second cam 334 in a second direction. In some embodiments, the first direction is opposite the second direction.

Figure 17:
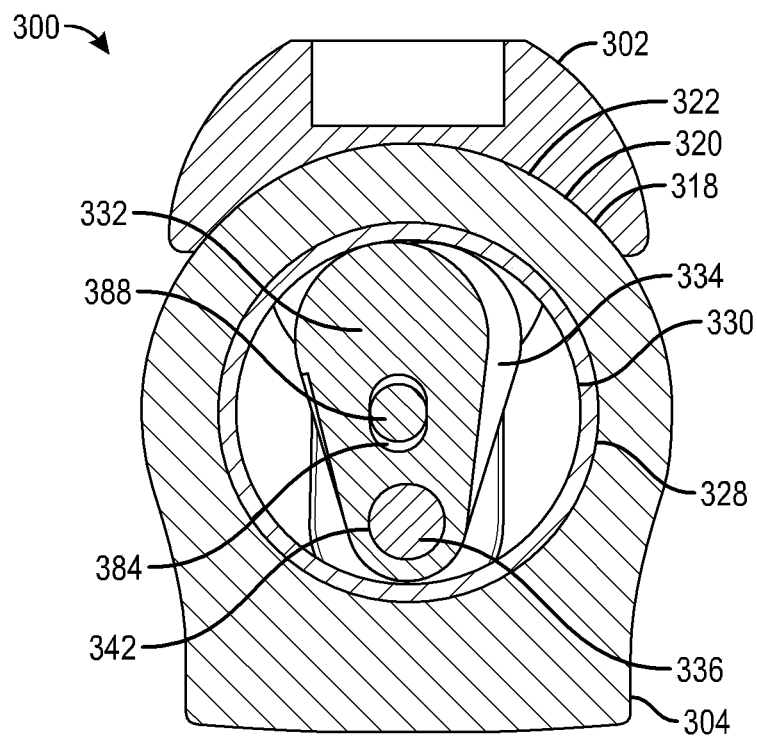
FIG. 17 is a cross-sectional side view of the prosthetic joint of FIG. 15 in the locked configuration.

FIGS. 15-19 show the prosthetic joint 300 in the locked configuration. In the locked configuration, a proximal portion 366 of the first cam 332 makes contact with, abut, or otherwise touch the cylindrical track 330 of the cylindrical chamber 328 as shown in FIG. 17. The turnkey 378 has the first pin portion 388 disposed within the first turnkey cam hole 384 of the first cam 332. The turnkey 378 has the second pin portion 390 disposed within the second turnkey cam hole 386 of the second cam 334. In the locked configuration, the first pin portion 388 of the turnkey 378 is laterally offset from the second pin portion 390 of the turnkey 378. The first pin portion 388 of the turnkey 378 and the second pin portion 390 of the turnkey 378 are not aligned along an axis parallel to the width of the prosthetic joint 300. The first pin portion 388 of the turnkey 378 and the second pin portion 390 of the turnkey 378 are not aligned along an axis parallel to the axle 336. The first pin portion 388 of the turnkey 378 and the second pin portion 390 of the turnkey are not aligned along an axis perpendicular to the first distally extending arm 314 or the second distally extending arm 316.

In some embodiments, in the locked configuration, the first cam 332 and the second cam 334 form a V-shape. At least a portion of the first cam 332 is laterally offset from the second cam 334. For instance, a proximal portion 366 of the first cam 332 can be laterally offset from a proximal portion 368 of the second cam 334. The first attachment member 302 is substantially prevented from rotating in the first direction because the first cam 332 cannot rotate further with respect to the cylindrical chamber 328 and/or the cylindrical track 330. The first attachment member 302 is inhibited (e.g., prevented) from rotating in the second direction because the second cam 334 cannot rotate further with respect to the cylindrical chamber 328 and/or the cylindrical track 330.

The first cam spring 356 biases the first cam 332 into contact with the turnkey 378. The second cam spring 358 biases the second cam 334 into contact with the turnkey 378. The turnkey 378 applies a force to the first cam 332 in a first direction, out of alignment with the second cam 334. The turnkey 378 applies a force to the second cam 334 in a second direction, out of alignment with the first cam 332. In the locked configuration, a proximal portion 366 of the first cam 332 and a proximal portion 368 of the second cam 334 make contact with, abut, or otherwise touch the cylindrical track 330 of the cylindrical chamber 328.

FIGS. 20-23 show the prosthetic joint 300 in the unlocked configuration. To unlock the prosthetic joint 300, a handle 396 of the turnkey 378 is rotated. For instance, the handle 396 can be horizontal when the prosthetic joint 300 is locked and vertical when the prosthetic joint 300 is unlocked. In some embodiments, the turnkey 378 is rotated 90 degrees between the locked and unlocked configurations. However, other configurations are contemplated (e.g., other angles between the locked and unlocked configurations). In the unlocked configuration, the first portion 388 of the turnkey 378 is aligned the second portion 390 of the turnkey 378. The first pin portion 388 of the turnkey 378 and the second pin portion 390 of the turnkey 378 are aligned along an axis parallel to the width of the prosthetic joint 300. The first pin portion 388 of the turnkey 378 and the second pin portion 390 of the turnkey 378 are aligned along an axis parallel to the axle 336. The first pin portion 388 of the turnkey 378 and the second pin portion 390 of the turnkey are aligned along an axis perpendicular to the first distally extending arm 314 or the second distally extending arm 316.

The first cam spring 356 biases the first cam 332 into contact with the turnkey 378. The second cam spring 158 biases the second cam 334 into contact with the turnkey 378. The first cam spring 356 applies a force to the first cam 332 in a first direction, into alignment with the second cam 334. The first cam spring 356 applies a force to the second cam 334 in a second direction, into of alignment with the first cam 332.

In the unlocked configuration, the proximal portion 366 of the first cam 332 may not make contact with, abut, or otherwise touch the cylindrical track 330 of the cylindrical chamber 328. In the unlocked configuration, the proximal portion 368 of the second cam 334 may not make contact with, abut, or otherwise touch the cylindrical track 330 of the cylindrical chamber 328.

In the unlocked configuration, the first attachment member 302 can rotate with respect to the second attachment member 304. In this configuration, the first cam 332, the second cam 334, first cam spring 356, and second cam spring 358 do not resist rotational movement. The first attachment member 302 including the first distally extending arm 314 and the second distally extending arm 316, the axle 336, the first cam 332, the second cam 334 and the turnkey 378 can rotate as a unit with respect to the second attachment member 304. In the unlocked configuration, the first cam 332 and the second cam 334 can be rotated within the cylindrical track 330 of the cylindrical chamber 328. In the unlocked configuration, the first attachment member 302 can be rotated to different orientations with respect to the second attachment member 304.

After the desired orientation is reached, the turnkey 378 can be rotated to lock the orientation of the prosthetic joint 300. In some embodiments, the turnkey 378 is rotated 90 degrees. The turnkey 378 applies a force to the first cam 332 in a first direction, out of alignment with the second cam 334. The turnkey 378 applies a force to the second cam 334 in a second direction, out of alignment with the first cam 332. In the locked configuration, a proximal portion 366 of the first cam 332 and a proximal portion 368 of the second cam 334 make contact with, abut, or otherwise touch the cylindrical track 330 of the cylindrical chamber 328. In the locked configuration, the first attachment member 302 is inhibited (e.g., prevented) from rotating with respect to the second attachment member 304.

FIGS. 26-34 depict an embodiment of a prosthetic joint 400. The prosthetic joint 400 can have similar features to those described with respect to prosthetic joint 100, 200, or 300. The prosthetic joint 400 can include a first attachment member 402 and a second attachment member 404. The prosthetic joint 400 can attach to a user or to another prosthetic device with the first attachment member 402. The prosthetic joint 400 can attach to a user or to another prosthetic device with the second attachment member 404.

The first attachment member 402 is depicted as including a first connection portion 406 shown in the illustrated embodiment as a pyramid connector. The first connection portion 406 can in other embodiments include attachment features, such as a hole and pin, a threaded hole or screw, a latch, a magnetic member, tube clamp, or other features. In some embodiments, the second attachment member 404 includes a second connection portion 408. The second connection portion 408 can include a pyramid connector, a hole and pin, a threaded hole or screw, a latch, a magnetic member, tube clamp, or other features.

Figure 28:
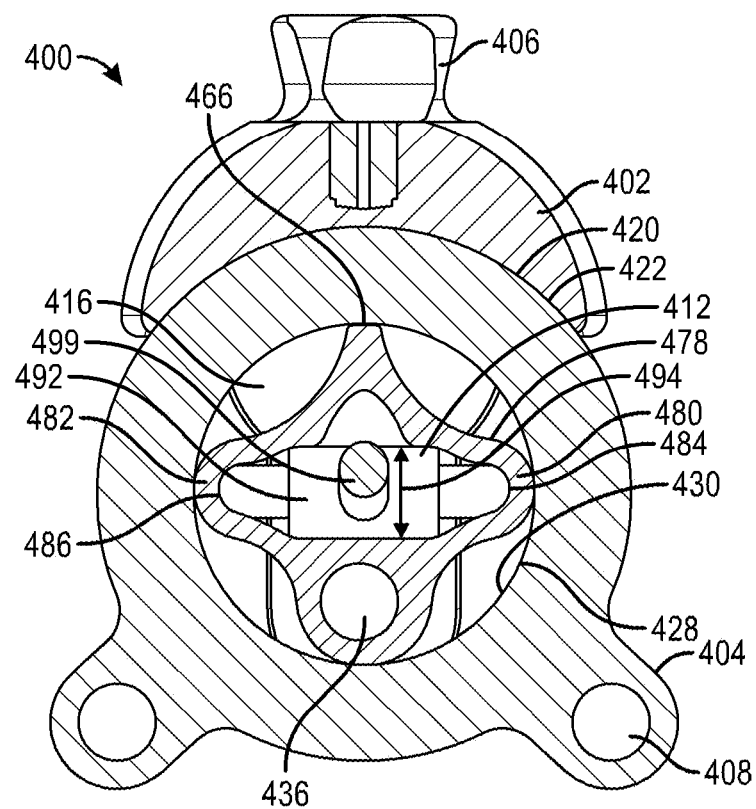
FIG. 28 is a cross-sectional side view of the prosthetic joint of FIG. 26 in the locked configuration.
Figure 29:
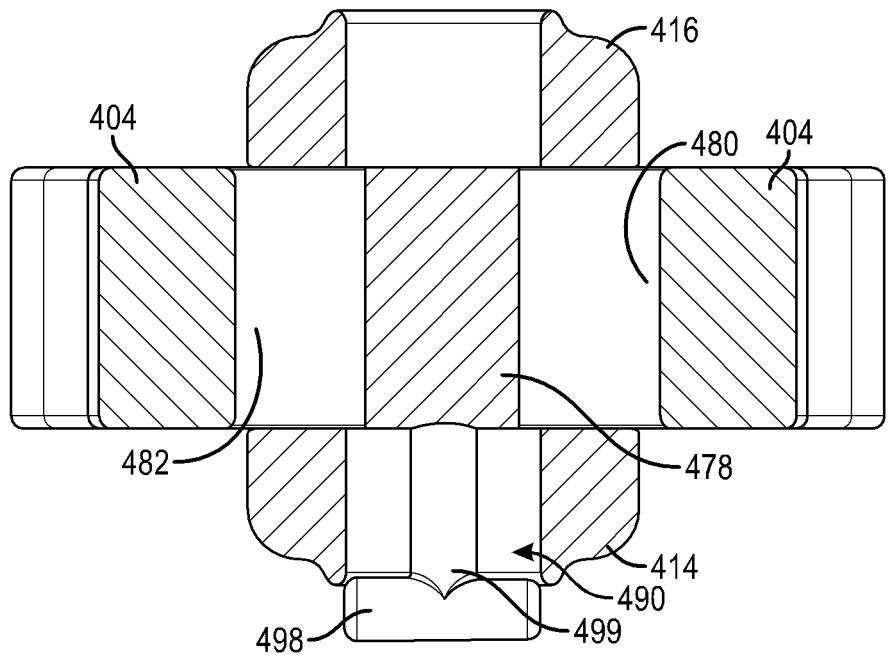
FIG. 29 is a cross-sectional top view of the prosthetic joint of FIG. 26 in the locked configuration.
Figure 30:
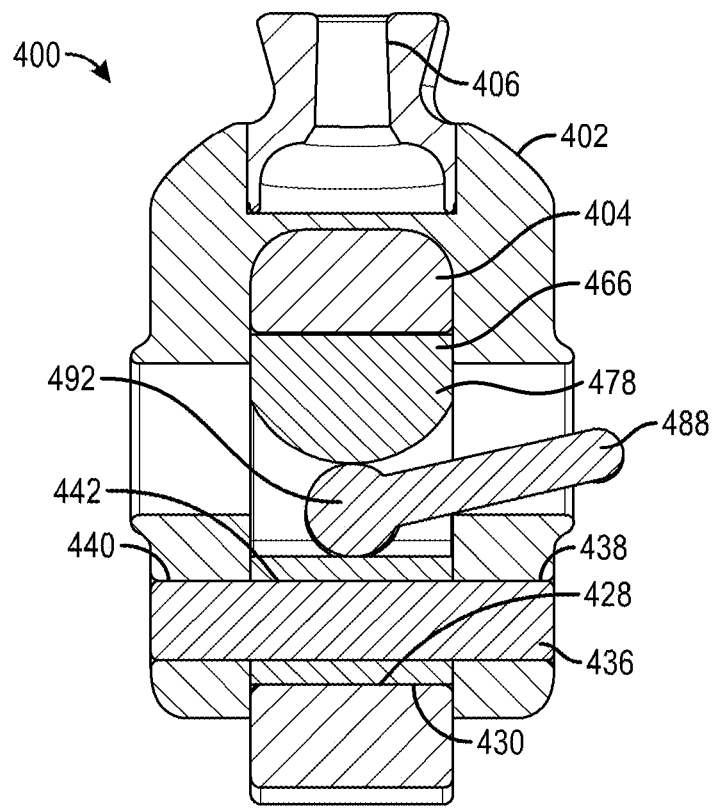
FIG. 30 is a transverse cross-sectional view of the prosthetic joint of FIG. 26 in the locked configuration.
Figure 31:
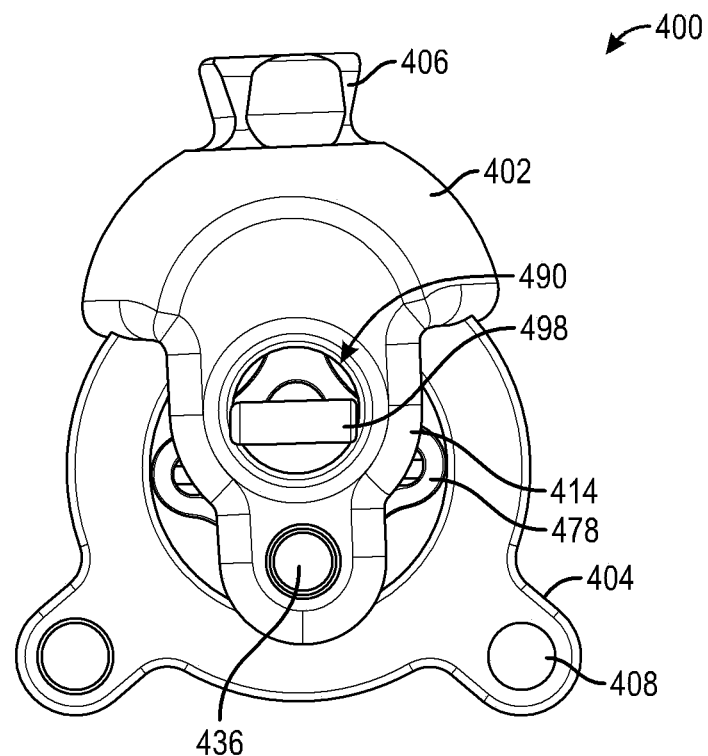
FIG. 31 is a side view of an embodiment of the prosthetic joint of FIG. 26 in the unlocked configuration.

In some embodiments, the first attachment member 402 can include a first distally extending arm 414 and a second distally extending arm 416. In between the distally extending arms 414 and 416, the first attachment member 402 can have a space 418 sized to accept the second attachment member 404. The space 418 can permit the first attachment member 402 and the second attachment member 404 to rotate relative to each other. The space 418 can be defined by an inner surface of the first distally extending arm 414, an inner surface of the second distally extending arm 416, and an inner surface 420. The inner surface 420 can be curved or concave as shown in FIG. 28. In some embodiments, the second attachment member 404 can include a curved or convex outer surface 422. The inner surface 120 of the first attachment member 102 can permit the outer surface 122 of the second attachment member 104 to rotate thereon.

As shown in FIG. 28, the second attachment member 404 can include a cylindrical chamber 428. The cylindrical chamber 428 can define a cylindrical track 430. The prosthetic joint 400 can include one or more cams. In the illustrated embodiment, the cams include a cam 478. FIGS. 26-34 depict the cam 478, but one cam or a plurality of cams can be utilized. The cam 478 is sized to fit within the cylindrical chamber 428 of the second attachment member 404. For instance, the cam 478 can have a smaller width than the cylindrical chamber 428. When the prosthetic joint 400 is assembled, the first attachment member 402 is coupled to the second attachment member 404 at least partially via the cam 478. In the illustrated embodiment, the cam 478 can be diamond shaped. The cam 478 has a proximal portion 466, a first side portion 480, and a second side portion 482. In some embodiments, the first side portion 480 can include a side hole 484. The second side portion 482 can include a side hole 486. In some embodiments, the first side portion 480 contacts the cylindrical track 430. In some embodiments, the second side portion 482 contacts the cylindrical track 430.

The first attachment member 402 can provide a rotatable connection with the second attachment member 404. The first attachment member 402 can include an axle 436. In some embodiments, the axle 436 passes through a first hole 438 in the first distally extending arm 414. In some embodiments, the axle 436 passes through a second hole 440 in the second distally extending arm 416. In some embodiments, the cam 478 can include or define a first cam hole 442 (see FIG. 30). In the illustrated embodiment, the axle 436 passes through a first hole 438 in the first distally extending arm 414, the first cam hole 442 in the cam 478, and the second hole 440 in the second distally extending arm 416 respectively. The first distally extending arm 414, the second distally extending arm 416, and the axle 436 can be rigidly coupled. In some embodiments, the first distally extending arm 414, the second distally extending arm 416, and the cam 478 can be rigidly coupled.

The prosthetic joint 100 can include one or more unlocking members. In the illustrated embodiment, the unlocking member includes a positioning lever 488. The first distally extending arm 414 can include a lever hole 490. The positioning lever 488 can make contact with, abut, or otherwise touch the cam 478. In some embodiments, the positioning lever 488 is partially received within the side hole 484 of the first side portion 480. In some embodiments, the positioning lever 488 is partially received within the side hole 486 of the second side portion 442. The positioning lever 488 can rotate with respect to the side holes 480, 482. In some embodiments, an extension 499 connected to the positioning lever 488 is partially received within the lever hole 490. The extension 499 connected to the positioning lever 488 can rotate with respect to the lever hole 490.

Figure 32:
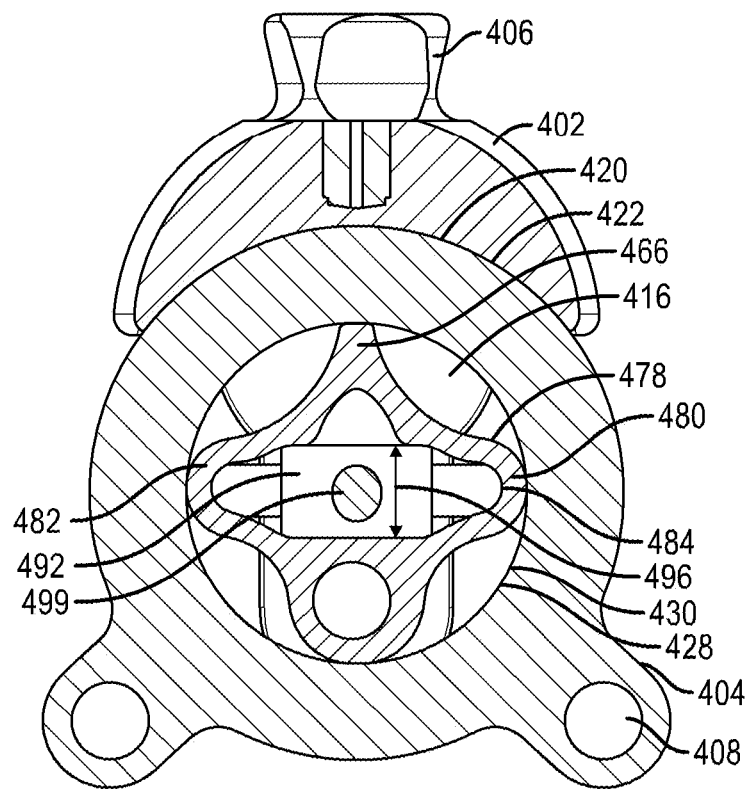
FIG. 32 is a cross-sectional side view of the prosthetic joint of FIG. 26 in the unlocked configuration.
Figure 33:
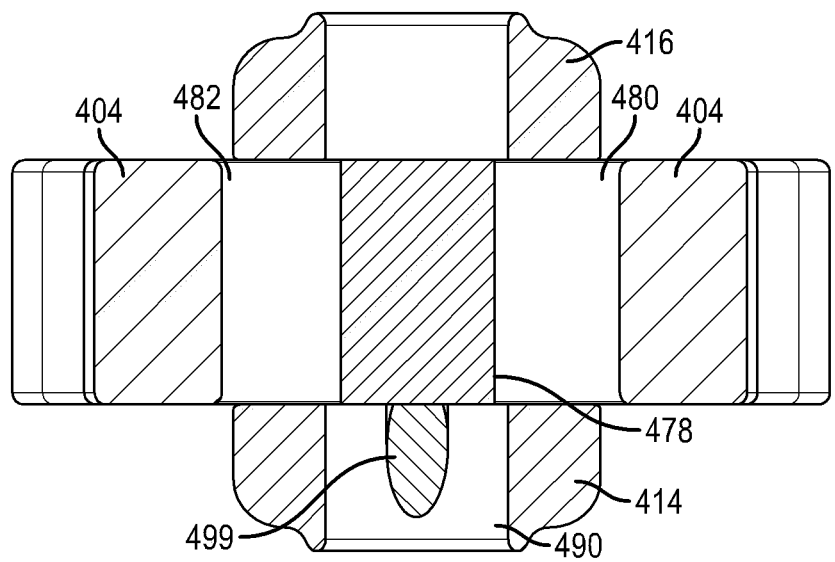
FIG. 33 is a cross-sectional top view of the prosthetic joint of FIG. 26 in the unlocked configuration.
Figure 34:
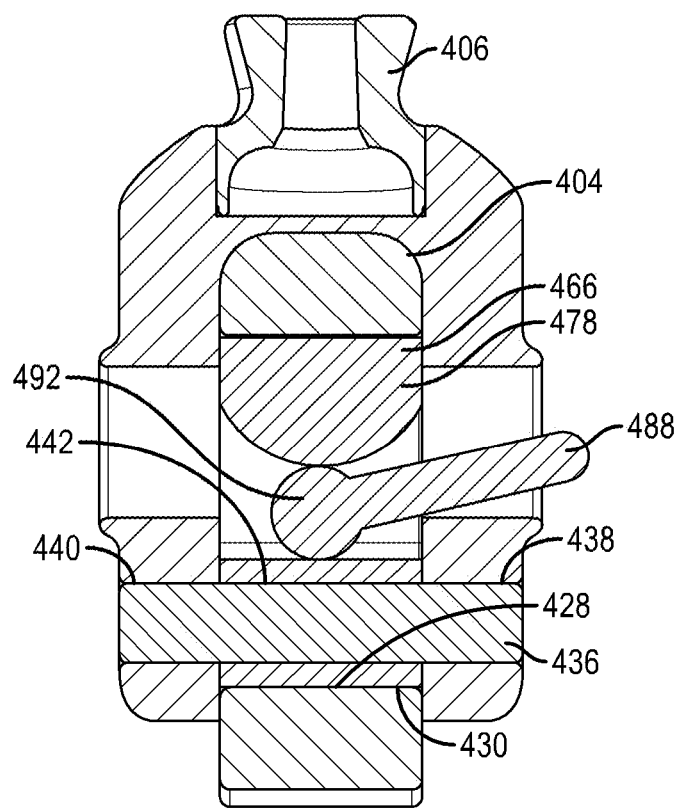
FIG. 34 is a transverse cross-sectional view of the prosthetic joint of FIG. 26 in the unlocked configuration.
Figure 35:
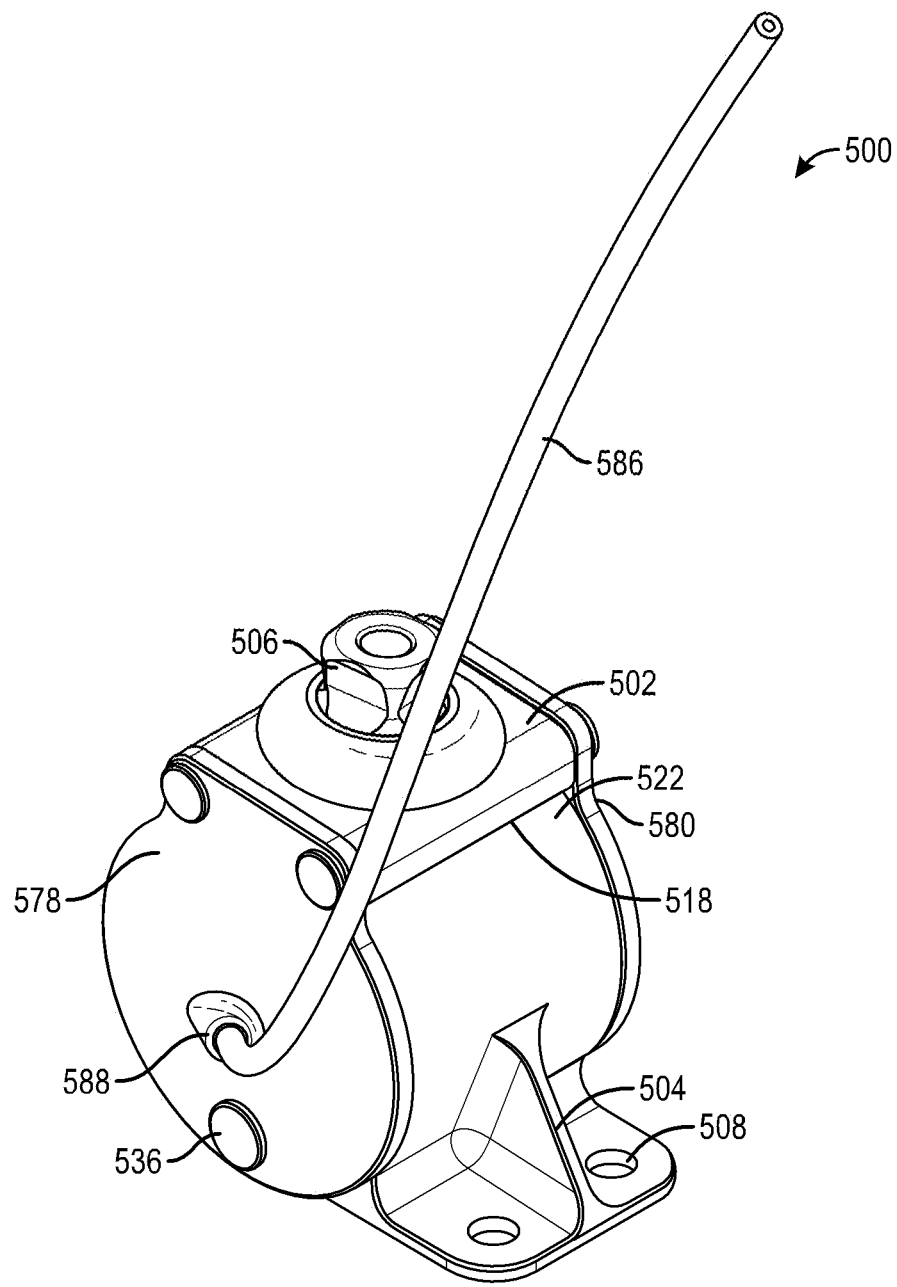
FIG. 35 is a perspective view of an embodiment of a prosthetic joint.
Figure 36:
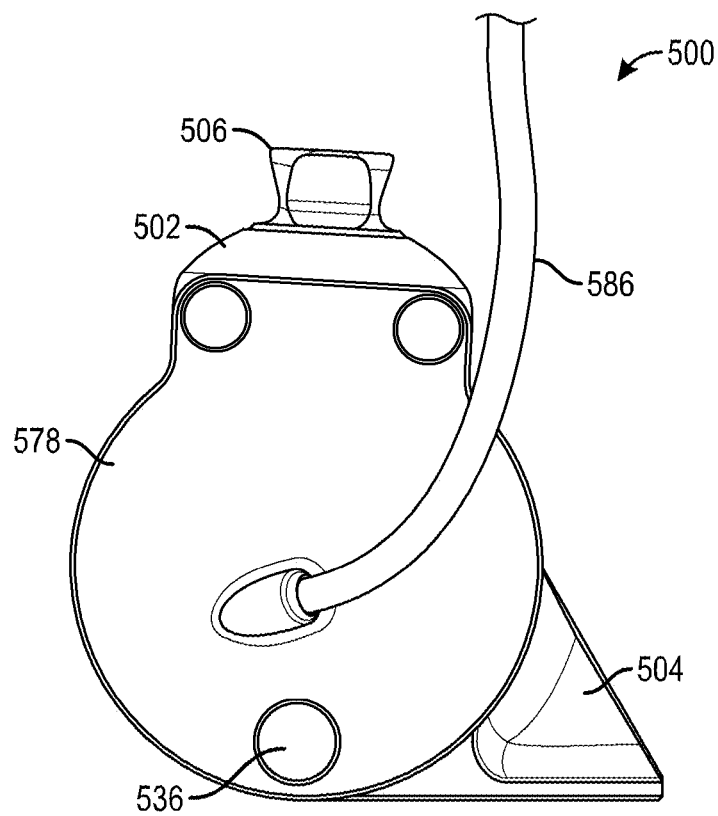
FIG. 36 is a side view of the prosthetic joint of FIG. 35 in the locked configuration.

The positioning lever 488 can include an engagement portion 492. The engagement portion 492 can be disposed between the sides 480, 482 of the cam 478. The engagement portion 492 can be disposed between the side holes 484, 486 of the cam 478. The engagement portion 492 can be disposed below the proximal portion 466 of the cam 478. As shown in FIG. 28, the engagement portion 492 can have a first dimension 494. The constant first dimension 494 can be along an axis that is perpendicular to the width of the prosthetic joint 400. As shown in FIG. 32, the engagement portion 492 can have a second dimension 496. The second dimension 496 can be along an axis that is perpendicular to the width of the prosthetic joint 400. In some embodiments, the second dimension 496 can be less than the first dimension 494. When the first dimension 492 is in contact with the cam 478, the prosthetic joint 400 is in the locked configuration. When the second dimension 494 is in contact with the cam 478, the prosthetic joint 400 is in the unlocked configuration. The first dimension 494 can be circumferentially offset (e.g., by 15 degrees, 30 degrees, etc.) form the second dimension 496 along the engagement portion 492.

FIGS. 26-30 show the prosthetic joint 300 in the locked configuration. In the locked configuration, a proximal portion 466 of the cam 478 makes contact with, abut, or otherwise touch the cylindrical track 430 of the cylindrical chamber 428. The positioning lever 488 is at least partially disposed within the side hole 484 of the first side 480. The positioning lever 488 is at least partially disposed within the side hole 486 of the second side 482. The first dimension 494 of the engagement portion 492 is circumferentially offset from the second dimension 496. In the locked configuration, the first dimension 494 of the engagement portion 492 can be in contact with the cam 478. In the locked configuration, the second dimension 496 of the engagement portion 492 may not be in contact with the cam 478. For instance, the second dimension 496 of the engagement portion 492 may face toward one of the distally extending arms 414, 416.

The engagement portion 492 of the positioning lever 488 applies a force to the cam 478 in a direction toward the cylindrical track 430 of the cylindrical chamber 428. In the illustrated embodiment, the cam 478 is sufficiently flexible to be pushed by the engagement portion 492 of the positioning lever 488. The cam 478 can be designed to avoid stress or fracture points from repeatedly bending. In some embodiments, the flexibility of the cam 478 is attributable to the shape of the cam 478. In some embodiments, the flexibility of the cam 478 is attributable to the material of the cam 478 (e.g., a resilient material). The proximal portion 466 of first cam 478 reversibly flexes toward the cylindrical chamber 428. In the locked configuration, a proximal portion 466 of the cam 478 makes contact with, abut, or otherwise touch the cylindrical track 430 of the cylindrical chamber 428.

FIGS. 31-34 show the prosthetic joint 400 in the unlocked configuration. To unlock the prosthetic joint 400, a handle 498 of the positioning lever 488 is rotated. For instance, the handle 498 can be near the proximal end when the prosthetic joint 400 is locked and near the distal end when the prosthetic joint 400 is unlocked. In some embodiments, the positioning lever 488 is rotated 90 degrees. Other configurations (e.g., angles to which the positioning lever 488 is rotated) are contemplated.

The first dimension 494 of the engagement portion 492 is circumferentially offset from the second dimension 496. In the unlocked configuration, the second dimension 496 of the engagement portion 492 can be in contact with the cam 478. In the unlocked configuration, the first dimension 494 of the positioning lever 488 may not be in contact with the cam 478. For instance, the first dimension 494 of the engagement portion 492 may face toward one of the distally extending arms 414, 416. The second dimension 496 can be less than the first dimension 494 of the engagement portion 492.

In the unlocked configuration, the proximal portion 466 of the cam 478 may not make contact with, abut, or otherwise touch the cylindrical track 430 of the cylindrical chamber 428. In some embodiments, the shape or material of the cam 478 biases the first cam 332 out of engagement of the cylindrical track 430. In some embodiments, the shape or material of the cam 478 biases the first cam 332 into contact with the engagement portion 492.

In the unlocked configuration, the first attachment member 402 is permitted to rotate with respect to the second attachment member 404. In this configuration, the cam 478 does not resist rotational movement. The first attachment member 402 and the second attachment member 404 can rotate relative to each other. The first attachment member 402 including the first distally extending arm 414 and the second distally extending arm 416, the axle 436, the cam 478, and the positioning lever 488 can rotate as a unit with respect to the second attachment member 404. In the unlocked configuration, the cam 478 can be rotated within the cylindrical track 430 of the cylindrical chamber 428. In the unlocked configuration, the first attachment member 402 can be rotated to different orientations with respect to the second attachment member 404.

After the desired orientation is reached, the positioning lever 488 can be rotated to lock the orientation of the prosthetic joint 400. In some embodiments, the positioning lever 488 is rotated 90 degrees. In other embodiments, the positioning lever 488 can be rotated 60 degrees, 30 degrees, 15 degrees, etc. The engagement portion 492 applies a force to the cam 478 toward the cylindrical track 430 of the cylindrical chamber 428. The proximal portion 466 of the cam 478 can make contact with, abut, or otherwise touch the cylindrical track 430 of the cylindrical chamber 428. In the locked configuration, the first attachment member 402 is prohibited or substantially prohibited from rotating with respect to the second attachment member 404.

FIGS. 35-42 depict an embodiment of a prosthetic joint 500. The prosthetic joint 500 can have similar features to those described with respect to prosthetic joint 100, 200, 300, or 400. The prosthetic joint 500 can include a first attachment member 502 and a second attachment member 504. The prosthetic joint 500 can attach to a user or to another prosthetic device with the first attachment member 502. The prosthetic joint 500 can attach to a user or to another prosthetic device with the second attachment member 504.

The first attachment member 502 is depicted as including a first connection portion 506 shown in the illustrated embodiment as a pyramid connector. The first connection portion 506 can in other embodiments include attachment features other than a pyramid connector, such as a hole and pin, a threaded hole or screw, a latch, a magnetic member, tube clamp, or other features. In some embodiments, the second attachment member 504 includes a second connection portion 508. The second connection portion 508 can include a pyramid connector, a hole and pin, a threaded hole or screw, a latch, a magnetic member, tube clamp, or other features.

In some embodiments, the first attachment member 502 can include a first distally extending lid 578 and a second distally extending lid 580. In some embodiments, the first distally extending lid 578 can be identical, substantially similar or a mirror image of the second distally extending lid 580. In some embodiments, the first distally extending lid 578 can have additional features, for instance holes, than the second distally extending lid 580. The prosthetic joint 500 can include a first distally extending lid 578 and a second distally extending lid 580 that can be positioned on opposite sides of the first attachment member 502.

In between the distally extending lids 578, 580, the first attachment member 502 can have a space 518 sized to accept the second attachment member 504. The space 518 can permit the first attachment member 502 and the second attachment member 504 to rotate relative to each other. The space 518 can be defined by an inner surface of the first distally extending lid 578, an inner surface of the second distally extending lid 580, and an inner surface 520. The inner surface 520 can be curved or concave. In some embodiments, the second attachment member 504 can include a curved or convex outer surface 522. The inner surface 520 of the first attachment member 502 can provide a bearing surface for the outer surface 522 of the second attachment member 504.

Figure 37:
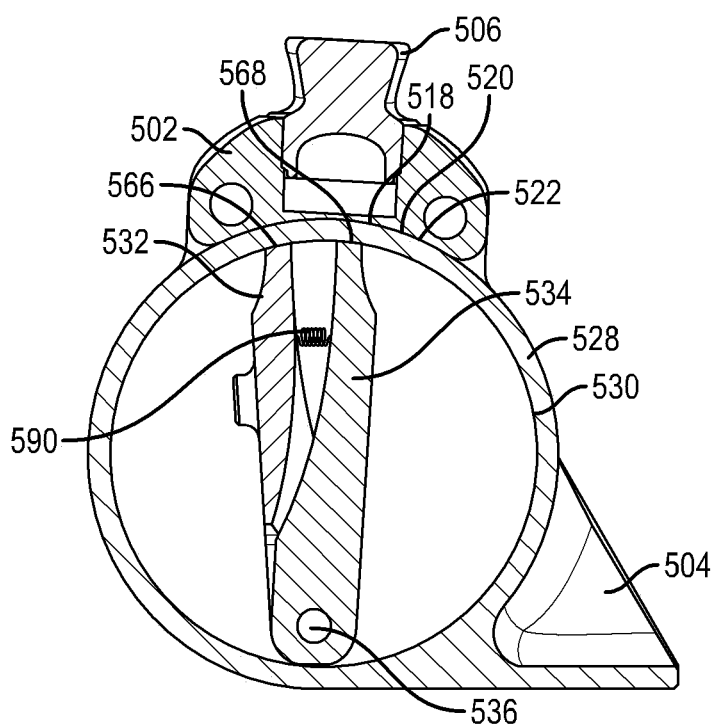
FIG. 37 is a cross-sectional side view of the prosthetic joint of FIG. 35 in the locked configuration.
Figure 38:
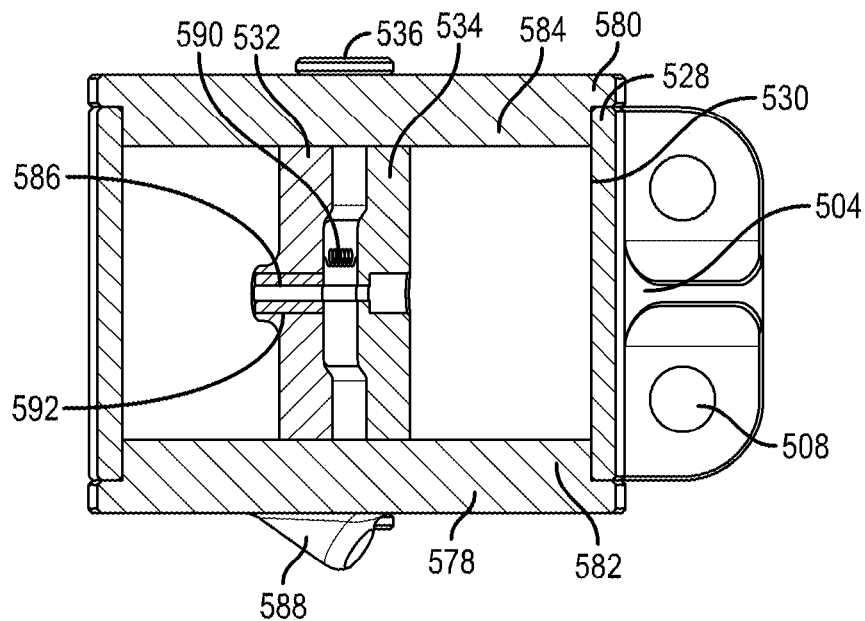
FIG. 38 is a cross-sectional top view of the prosthetic joint of FIG. 35 in the locked configuration.

As shown in FIG. 37, the second attachment member 504 can include a cylindrical chamber 528. The cylindrical chamber 528 can define a cylindrical track 530. As shown in FIG. 38, the distally extending lid 578 can include a first sidewall 582 and the distally extending lid 580 can include a second sidewall 584. The sidewalls 582, 584 can be sized to fit inside the cylindrical chamber 528 of the second attachment member 504. The first sidewalls 582 of the first distally extending lid 478 can provide a bearing surface for the cylindrical chamber 528. The second sidewalls 582 of the second distally extending lid 580 can provide a bearing surface for the cylindrical chamber 528. The cylindrical chamber 528 and the sidewalls 582, 584 can provide a more robust connection between the first attachment member 502 and the second attachment member 504. The inner surface of the cylindrical chamber 528 can extend against the outer surface of the first sidewall 582. The inner surface of the cylindrical chamber 528 can extend against the outer surface of the second sidewall 584.

When the prosthetic joint 500 is assembled, the sidewalls 582, 584 of the distally extending lids 578, 580 can be received within the cylindrical chamber 528 of the second attachment member 504. The distally extending lids 578, 580 that fit inside the cylindrical chamber 528 will make it possible to maximize the length and width of the cams 532, 534 compared to other joints described herein. The increased length of the cams 532, 534 results in better strength and security of the prosthetic joint 500. In some embodiments, the cylindrical chamber 528 is insertable within the distally extending lids 578, 580. The insertable cylindrical chamber 528 makes it possible to increase the width of the cams 532, 534 without making the complete prosthetic joint 500 wider. The insertable cylindrical chamber 528 makes it possible to reduce the weight of the prosthetic joint 500.

The prosthetic joint 500 can include one or more cams. In the illustrated embodiment, the cams include a first cam 532 and a second cam 534. The first cam 532 and the second cam 534 are sized to fit within the cylindrical chamber 528 of the second attachment member 504. For instance, the first cam 532 and the second cam 534 can each have a smaller width than the cylindrical chamber 528. The first cam 532 and the second cam 534 can be sized to fit within the cylindrical chamber 528 less the distance occupied by the sidewalls 582, 584. The first cam 532 and the second cam 534 can be sized to fit within the second attachment member 504. For instance, the first cam 532 and the second cam 534 can each have a smaller width than second attachment member 504. The first cam 532 can have a proximal portion 566. The proximal portion 566 can extend along the width of the cylindrical chamber 528 less the distance occupied by the sidewalls 582, 584. The proximal portion 566 can have greater surface contact with the cylindrical track 530 of the cylindrical chamber 528 than other cams described herein. The second cam 534 can have a proximal portion 568. The proximal portion 568 can extend along the width of the cylindrical chamber 528 less the distance occupied by the sidewalls 582, 584. The proximal portion 568 can have greater surface contact with the cylindrical track 530 of the cylindrical chamber 528 than other cams described herein. The wider first cam 532 and wider second cam 534 can have more friction with the cylindrical track 530 of the cylindrical chamber. The wider first cam 532 and wider second cam 534 can take more load. The cams 532, 534 can apply greater friction force (due to their increased area of contact) when engaged with cylindrical track 530. The prosthetic joint 500 can receive a greater load while maintaining the locked configuration relative to other prosthetic joints.

The first distally extending lid 578 can be coupled to the first attachment member 502. The second distally extending lid 580 can be coupled to the first attachment member 502. In the illustrated embodiment, a pair of fasteners passes through the first distally extending lid 578, the first attachment member 502, and second distally extending lid 580. For instance, the head of the fasteners can be near the first distally extending lid 578 and the nut of the fasteners can be near the second distally extending lid 580. Other methods of fastening the first distally extending lid 578, the first attachment member 502, and second distally extending lid 580 are contemplated.

The first attachment member 502 can provide a rotatable connection with the second attachment member 504, as described above with respect to prosthetic joint 100. The first attachment member 502 can include an axle 536. The axle 536 can pass through the first distally extending lid 578 and the second distally extending lid 580. In some embodiments, the axle 536 passes through a first hole 538 in the first distally extending lid 578. In some embodiments, the axle 536 passes through a second hole 540 in the second distally extending lid 580. The first hole 538 can be near a distal end of the first distally extending lid 578 and the second hole 540 can be near a distal end of the second distally extending lid 580.

Figure 39:
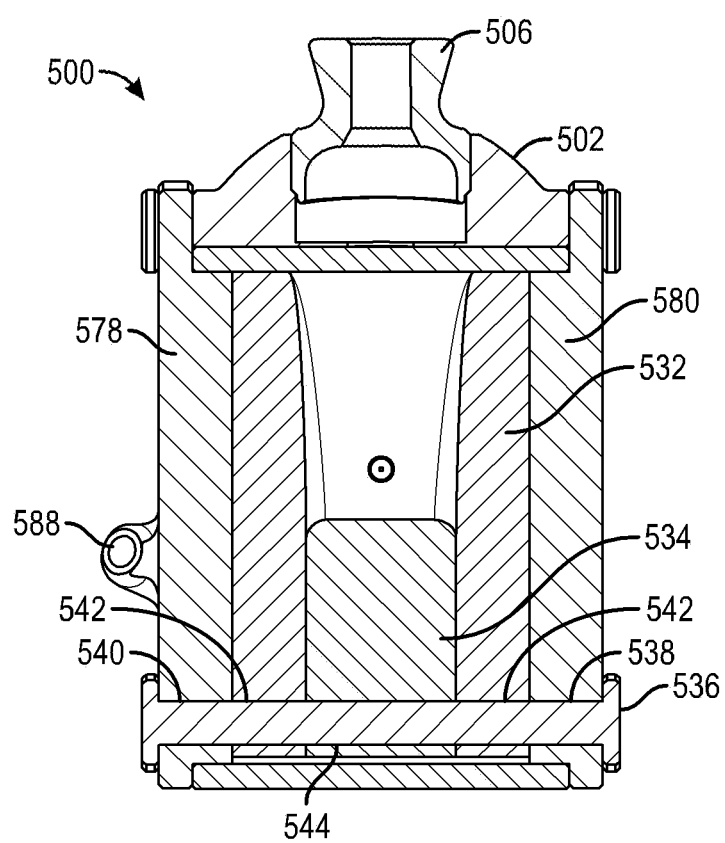
FIG. 39 is a transverse cross-sectional view of the prosthetic joint of FIG. 35 in the locked configuration.

In some embodiments, the first cam 532 can include or define one or more first cam holes 542 and the second cam 534 can include or define one or more second cam holes 544, as shown in FIG. 39. The axle 536 can extend through the first cam hole 542 and the second cam hole 544. In the illustrated embodiment, the first cam 532 includes two first cam holes 542 and the second cam 534 includes one second cam hole 544. The first cam 532 and the second cam 534 are interlaced along the axle 536. In the illustrated embodiment, the axle 536 passes through a first hole 538 in the first distally extending lid 578, a first cam hole 542 in the first cam 532, the second cam hole 544 in the second cam 534, another first cam hole 542 in the first cam 532, and the second hole 540 in the second distally extending lid 580 respectively. The first attachment member 502, first distally extending lid 578, the second distally extending lid 580, and the axle 536 can be rigidly coupled.

The prosthetic joint 500 can include one or more unlocking members. In the illustrated embodiment, the unlocking member includes a linear member 586 (e.g., a wire, such as a brake wire). In some embodiments, the linear member 586 is covered by tubing. The first distally extending lid 578 can include a hole 588. The hole 588 can allow the linear member 586 to extend through the first distally extending lid 578. The linear member 586 can extend into the cylindrical chamber 528. The linear member 586 can be coupled to the first cam 532, the second cam 534 or both the first cam 532 and the second cam 534.

The prosthetic joint 500 can include one or more biasing member. In the illustrated embodiment, the biasing member includes spring 590. The spring 590 can be located between the first cam 532 and the second cam 534. The first end of the spring 590 can be coupled to the first cam 532. The second end of the spring 590 can be coupled to the second cam 534. The spring 590 biases the first cam 532 in a first direction. The spring 590 biases the second cam 534 in a second direction. In a locked configuration, the spring 590 biases the cams 532, 534 out of alignment with each other. In a locked configuration, the spring 590 biases the cams 532, 534 apart. In other embodiments, two or more springs are used to bias the first cam 532 away from the second cam 534.

FIGS. 35-39 show the prosthetic joint 500 in the locked configuration. In the locked configuration, the proximal portion 566 of the first cam 532 makes contact with, abut, or otherwise touch the cylindrical track 530 of the cylindrical chamber 528. The spring 590 biases the first cam 532 into contact with the cylindrical track 530. The spring 590 biases the first cam 532 in a first direction, apart from the second cam 534. In the locked configuration, the proximal portion 568 of the second cam 534 makes contact with, abut, or otherwise touch the cylindrical track 530 of the cylindrical chamber 528. The spring 590 biases the second cam 534 into contact with the cylindrical track 530. The spring 590 biases the second cam 534 in a second direction, apart from the first cam 532. In the locked configuration, the proximal portion 566 of the first cam 532 and the proximal portion 568 of the second cam 534 make contact with, abut, or otherwise touch the cylindrical track 530 of the cylindrical chamber 528.

In some embodiments, in the locked configuration, the first cam 532 and the second cam 534 form a V-shape. At least a portion of the first cam 532 is laterally offset from the second cam 534. For instance, the proximal portion 566 of the first cam 532 can be laterally offset from a proximal portion 568 of the second cam 534. The first attachment member 502 is substantially prevented from rotating in the first direction because the first cam 532 cannot rotate further with respect to the cylindrical chamber 528 and/or the cylindrical track 530. The first attachment member 502 is inhibited (e.g., prevented) from rotating in the second direction because the second cam 534 cannot rotate further with respect to the cylindrical chamber 528 and/or the cylindrical track 530. In the locked configuration, the first attachment member 502 is prohibited or substantially prohibited from rotating with respect to the second attachment member 504.

Figure 40:
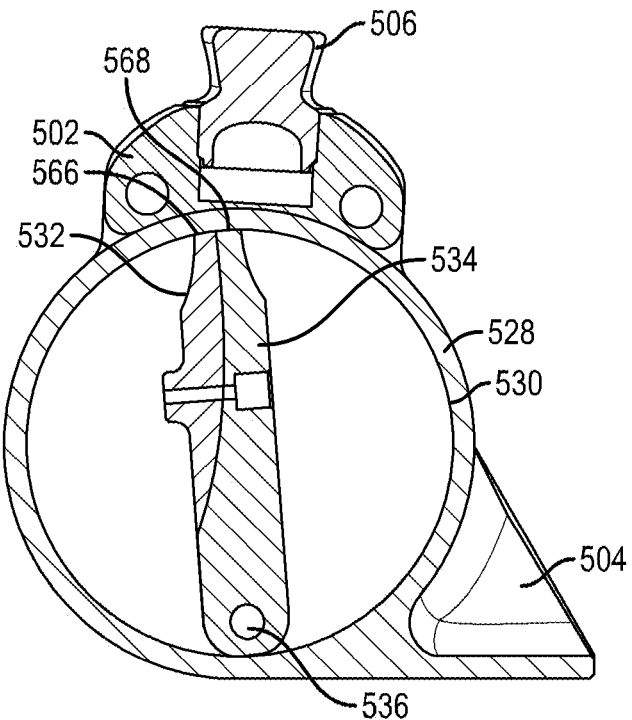
FIG. 40 is a cross-sectional side view of the prosthetic joint of FIG. 35 in the unlocked configuration.
Figure 41:
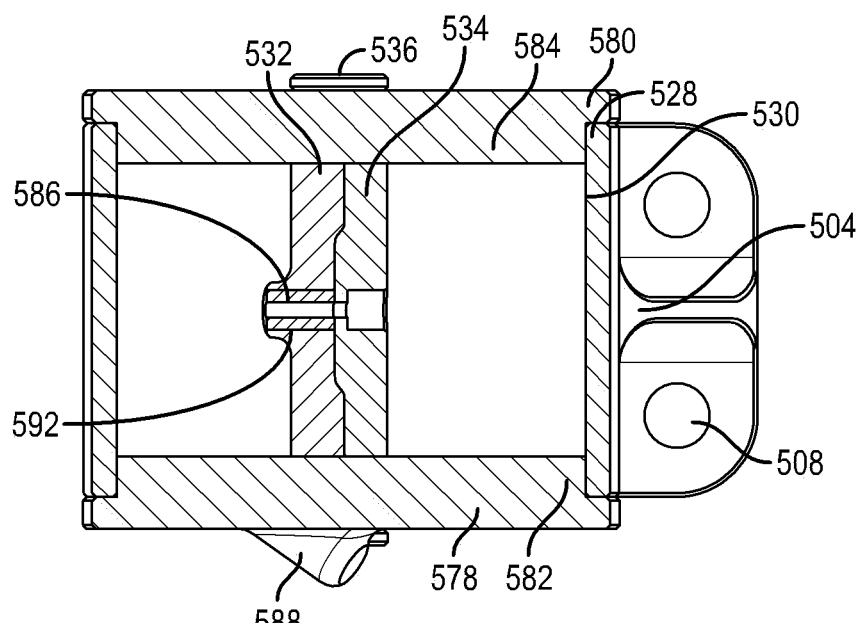
FIG. 41 is a cross-sectional top view of the prosthetic joint of FIG. 35 in the unlocked configuration.
Figure 42:
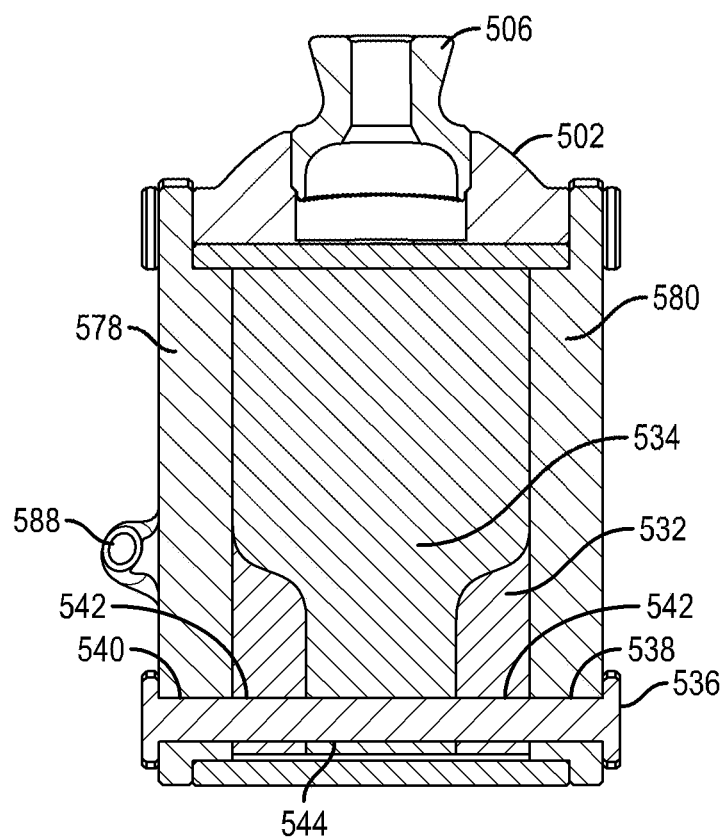
FIG. 42 is a transverse cross-sectional view of the prosthetic joint of FIG. 35 in the unlocked configuration.

FIG. 40-42 shows the prosthetic joint 500 in the unlocked configuration. To unlock the prosthetic joint 500, the linear member 586 is pulled. The linear member 586 can be pulled by the user (e.g., manually) or a device such as an external pump. The linear member 586 is coupled to one or both of the cams 532, 534. In the illustrated embodiments, the linear member 586 is coupled to the second cam 534. The linear member 586 passes through a hole 592 in the first cam 532. The action of pulling the linear member 586 pulls the second cam 534 toward the first cam 532. The linear member 586 slides through the hole 592 as the linear member 586 is pulled. In the some embodiments, the linear member 586 is coupled to the first cam 532 and passes through a hole in the second cam 534. The action of pulling the linear member 586 pulls the first cam 532 toward the second cam 534. The linear member 586 slides through the hole in the second cam 534 as the linear member 586 is pulled.

FIGS. 40-42 show the prosthetic joint 500 in the unlocked configuration. In the unlocked configuration, the proximal portion 566 of the first cam 532 may not make contact with, abut, or otherwise touch the cylindrical track 530 of the cylindrical chamber 528. In the unlocked configuration, the proximal portion 568 of the second cam 534 may not make contact with, abut, or otherwise touch the cylindrical track 530 of the cylindrical chamber 528. The biasing force of the spring 590 can be overcome. The second cam 534 can move in the first direction, toward the first cam 532. In some embodiments, the first cam 532 can remain stationary.

In the unlocked configuration, the first attachment member 502 is permitted to rotate with respect to the second attachment member 504. In this configuration, the first cam 532, the second cam 534 and the spring 590, do not resist rotational movement. The first attachment member 502, the first distally extending lid 578, the second distally extending lid 580, the first cam 532, the second cam 534, the axle 536, and the brake wire 586 can rotate as a unit with respect to the second attachment member 504. In the unlocked configuration, the first cam 532 and the second cam 534 can be rotated within the cylindrical chamber 528 and/or the cylindrical track 530. In the unlocked configuration, the first attachment member 502 can be rotated to different orientations with respect to the second attachment member 504.

After the desired orientation is reached, the linear member 586 can be released. In some embodiments, the spring 590 applies a force to the first cam 532 in a first direction, away from the second cam 534. In some embodiments, the spring 590 applies a force to the second cam 534 in a second direction, away from the first cam 532. In the locked configuration, the proximal portion 566 of the first cam 532 and the proximal portion 568 of the second cam 534 make contact with, abut, or otherwise touch the cylindrical track 530 of the cylindrical chamber 528.

Figure 24:
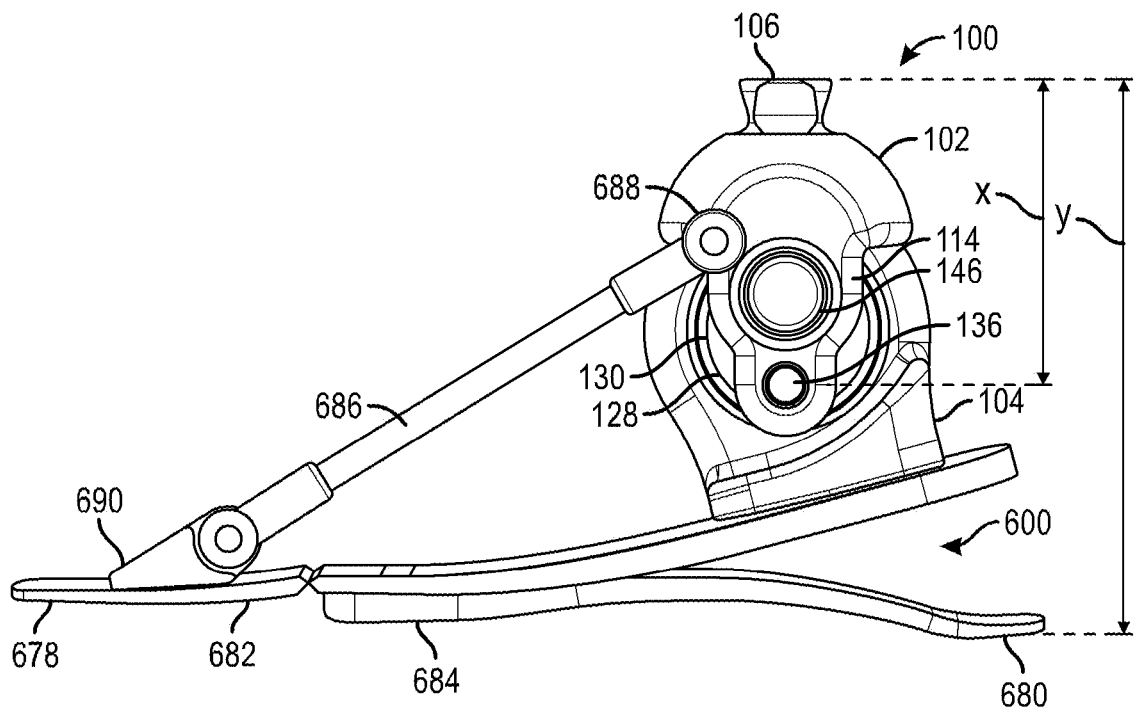
FIG. 24 is an embodiment of a prosthetic foot with a prosthetic joint of FIG. 1 in a low-heel configuration.
Figure 25:
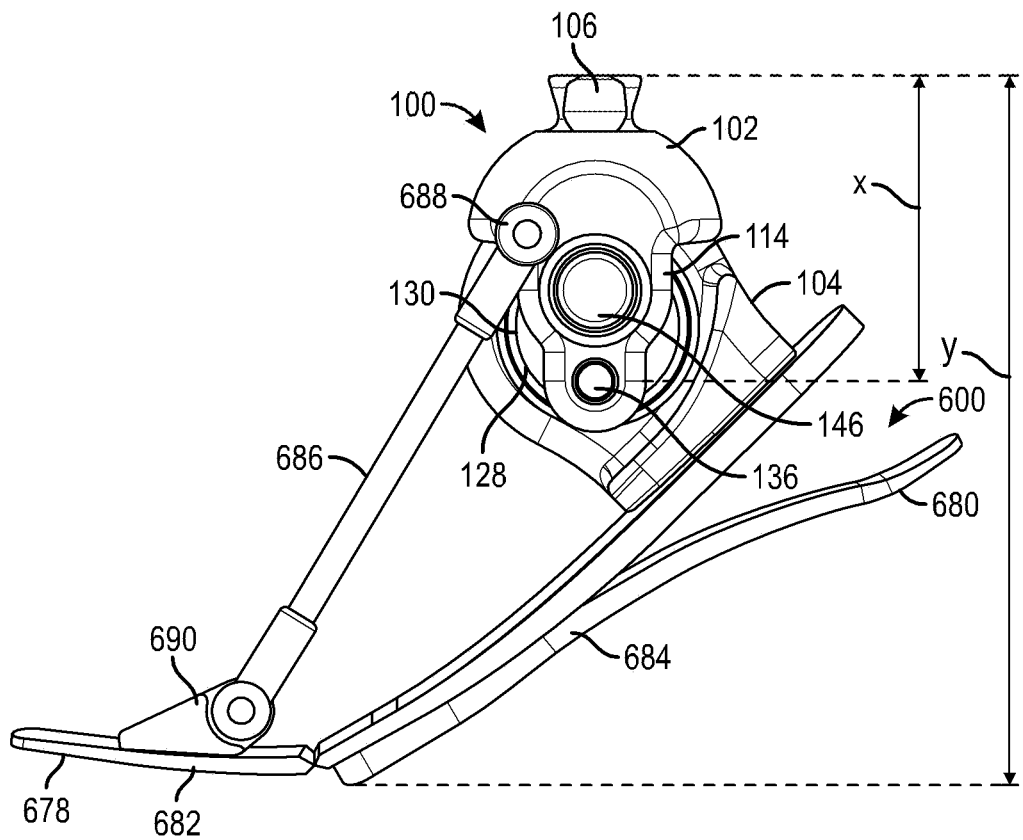
FIG. 25 is a different view of the prosthetic foot of FIG. 24 in a high-heel configuration.
Figure 26:
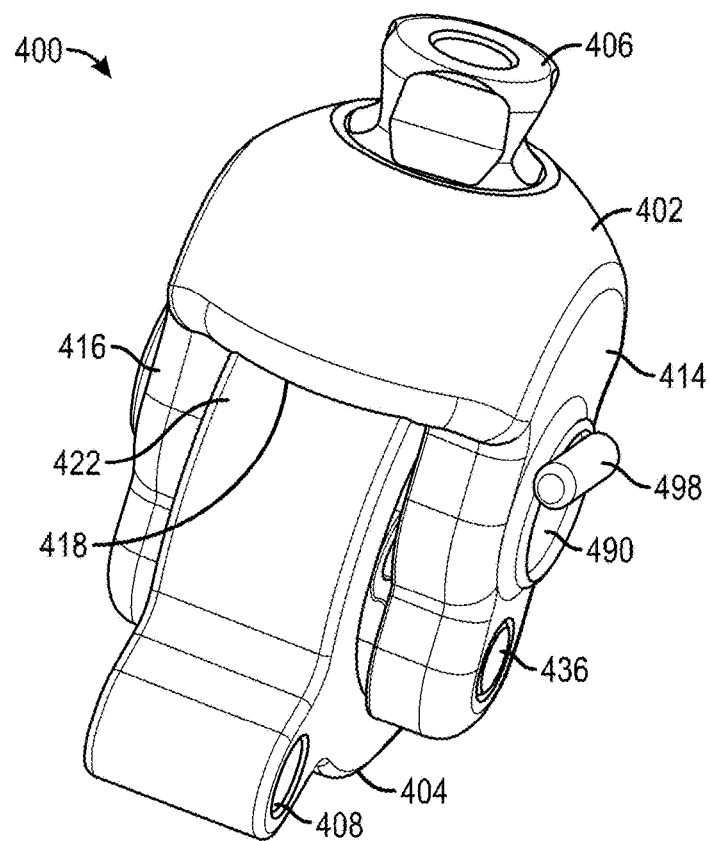
FIG. 26 is a perspective view of an embodiment of a prosthetic joint with a lever.
Figure 27:
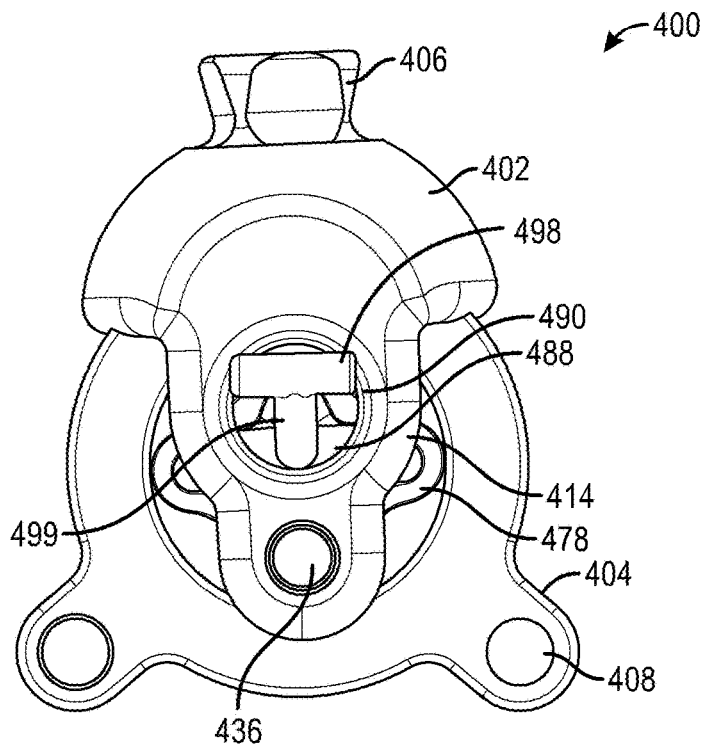
FIG. 27 is a side view of the prosthetic joint of FIG. 26 in the locked configuration.

As shown in FIGS. 24-25, the second attachment member 104 may be attached to a prosthetic foot 600. While the prosthetic joint 100 is shown, the prosthetic joint 200, 300, 400, or 500 may be attached to a prosthetic foot 600 in a similar manner. The first cam 132, the second cam 134, the first cam spring 156, and the second cam spring 158 can be mounted within the cylindrical chamber 128. The first cam 132 can be biased by the first cam spring 156 against the cylindrical track 130, in the locked configuration. The second cam 134 can be biased by the second cam spring 158 against the cylindrical track 130, in the locked configuration.

As shown in FIG. 24, the first attachment member 102 may be connected to the second attachment member 104. In some embodiments, the first attachment member 102 is placed over the second attachment member 104. As described above with respect to FIGS. 1-8, the axle 136 is passed through the first distally extending arm 114, the first cam 132, and the second cam 134, and the second distally extending arm 116. The first distally extending arm 114 can retain the first positioning member 146 and the second distally extending arm 116 can retain the second positioning member 148. The first positioning member 146, once retained within the first distally extending arm 114, can be in contact with the first cam 132. The second positioning member 148, once retained within the second distally extending arm 116, can be contact with the second cam 134. The first positioning member 146 and the second positioning member 148 can be depressed in order to bring the first cam 132 and the second cam 134 into alignment, thereby causing the prosthetic joint 100 to be in the unlocked configuration.

The first connection portion 106 is connected or integrally formed with the first attachment member 102. The first connection portion 106 and the first attachment member 102 can be aligned with a lower leg pylon (not shown). Any changes in the orientation of the joint 100 changes the angle of the second attachment member 104 relative to the first attachment member 102. Further, any changes in the orientation of the joint 100 changes the angle of the prosthetic foot 600 attached to the second attachment member 104 relative lower leg pylon attached to the first attachment member 102. By changing the orientation of the joint 100, the prosthetic foot 600 can be inclined upward or downward relative to the ground. The ability to change the inclination of the prosthetic foot 600 may be helpful to adjust the heel height of the prosthetic foot 600, therefore allowing the user to select footwear of various heel heights. Further, the ability to change the inclination of the prosthetic foot 600 may be useful, for example, when a user is walking up or down a constant grade.

As shown in FIG. 24, there is a set distance X between the first connection portion 106 and the axle 136. The distance X is fixed because the first distally extending arm 114 and second distally extending arm 116 are connected to the axle 136. Regardless of whether the prosthetic joint 100 is in the locked configuration or the unlocked configuration, the distance X remains unchanged.

As described above with respect to FIGS. 1-8, in the unlocked configuration, the axle 136, the first cam 132, the second cam 134, the first cam spring 156, and the second cam spring 158 can be rotated within the cylindrical track 130. The first attachment member 102 and the second attachment member 104 rotate with respect to each other. As shown in FIG. 24, the heel height is the distance Y between the first connection portion 106, and the planar contacting surface of the prosthetic foot 600.

As shown in FIG. 24, the prosthetic foot 600 can include a toe portion 678 and a heel portion 680. In some embodiments, the prosthetic foot 600 can include a first plate 682 and a second plate 684. The first plate 682 and the second plate 684 can form the contacting surface of the prosthetic foot 600. The second plate 684 can have a smaller length than the first plate 682. In some embodiments, the first plate 682 and the second plate 684 can separate near the heel portion 680 to have a distance there between.

The second connection portion 108 of the second attachment member 104 can couple to a proximal portion of the first plate 682. In some embodiments, the second attachment member 104 is located near the heel portion 680. The first attachment member 102 can be coupled to a connecting member 686. The connecting member 686 may couple the first attachment member 104 to the prosthetic foot 600, for example to the toe portion 678 of the prosthetic foot 600.

In some embodiments, the connecting member 686 provides a rigid coupling between the first attachment member 102 and the toe portion 678. This allows the user to adjust the toe portion 678 relative to the heel portion 680. The connecting member 686 may couple to any component of the first attachment member 102 including a proximal portion of the first attachment member 102, the first distally extending arm 114 or the second distally extending arm 116. The connecting member 686 can include a proximal end 688 coupled to the first attachment member 102. The connecting member 686 can include a distal end 690 coupled to the first plate 682. The distal end 690 of the connecting member 686 can be coupled to the toe portion 678. The proximal end 688 can include a coupling that can pivot with respect to the first attachment member 102. The distal end 690 can include a coupling that can pivot with respect to the prosthetic foot 600. The distal end 690 may be positioned in a location near the natural metatarsal joint on the prosthetic foot 600, in order to provide more natural movement. The distal end 690 may include spring components. The spring components may bias the prosthetic joint 100 towards either dorsiflexion or plantar flexion in a relaxed state In the unlocked configuration, the first attachment member 102 and the second attachment member 104 can rotate relative to each other. The connecting member 686 moves as a unit with the first attachment member 102. When the desired orientation is reached, the prosthetic joint 100 can be locked. The first attachment member 102 remains fixed to the toe portion 678 in both the unlocked and locked configuration. The second attachment member 104 remains fixed to the prosthetic foot 600 in both the unlocked and locked configuration. The angular position of the toe portion 678 can be adjusted relative to the heel portion 680 of the prosthetic foot 600 based on the tension applied by the connecting member 686.

The axle 136 can be positioned in a range of circumferential locations within the cylindrical chamber 128. There is one position where the heel height is a maximum. The maximum position is shown in FIG. 25. In this position, the first attachment member 102 is rotated rearward relative to the second attachment member 104. This motion rotates the connecting member 678 rearward since the connecting member 678 is coupled to first attachment member 102. This motion pulls on the toe portion 678 of the prosthetic foot 600 to lift the toe portion 678 relative to the heel portion 680 of the prosthetic foot 600.

Rotating the first attachment member 102 and the second attachment member 104 to a position other than the maximum position causes the heel height to decrease, as shown in FIG. 24. In this position, the first attachment member 102 is rotated upward relative to the second attachment member 104. This motion applies less force on the connecting member 678. The connecting member 678 relaxes the angle of the toe portion 678 of the prosthetic foot 600 relative to the heel portion 680 of the prosthetic foot 600.

In the range of circumferential locations, the first connection portion 106 remains in a vertical position, for instance to connect with the lower leg pylon. The first connection portion 106 generally extends along an axis substantially perpendicular to the contact surface of the toe portion 678. The range of circumferential location can be limited by the geometry of the system. In some embodiments, the range of locations is limited by the orientation of the first distally extending arm 114 and the second distally extending arm 116 with respect to the second attachment member 104. In some embodiments, the range of locations is limited by the orientation of the first distally extending arm 114 and the second distally extending arm 116 with respect to the prosthetic foot 600. In some embodiments, the range of locations is limited by the orientation of the curved, concave inner surface 120 of the first attachment member 102 and the curved, convex outer surface 122 of the second attachment member 104.

The connecting member 686 may be mechanical, electrical and/or pneumatic. For example, the connecting member 686 may include cable and pulley mechanism, roller mechanisms, and/or rigid linkages. The connecting member 686 provides added stability to support the prosthetic joint 100 in any heel height configuration. A longitudinal member of the connecting member 686 can be generally parallel to a segment of the prosthetic foot 600. In some embodiments, the longitudinal member of the connecting member 686 provides a load bearing surface in addition to the prosthetic foot 600. In some embodiments, the longitudinal member of the connecting member 686 is not be load bearing. In some embodiments, the longitudinal member of the connecting member 686 can be a mechanism that solely lifts the toe portion 678. In this embodiment, the load bearing mechanism may be inherent in the design of the bending portion of the prosthetic foot 600, such as the toe portion 678. In some embodiments, the bending portion of the prosthetic foot 600 can be made with a degree of resistance to bending (e.g., the toe portion 678 can be biased toward the down position, such as by a biasing spring). This resistance can be overcome by a pulling force connected to the ankle joint. This pulling force can in one embodiment be provided by the longitudinal member of the connecting member 686 for instance a shaft, cable mechanism, etc.

Typically, the user of the prosthetic device adjusts the prosthetic joint 100 by utilizing the positioning members 146, 148. By depressing the positioning members 148, 148 the prosthetic joint changes from the locked configuration to the unlocked configuration, as described herein. In other embodiments, the turnkey 378, the lever 488, the linear member 586 or other positioning member can be utilized. In some embodiment, a manufacturer provides the prosthetic joint 100 and instruction of use. The instructions of use can describe how the user can adjust the prosthetic joint 100.

As shown in FIGS. 43-46, the second attachment member 204 may be attached to a prosthetic foot 700. While the prosthetic joint 200 is shown, the prosthetic joint 100, 300, 400, or 500 may be attached to a prosthetic foot 700 in a similar manner. As described above with respect to FIGS. 9-14, the first cam 232, the second cam 234, the first cam spring 256, and the second cam spring 258 can be mounted within the cylindrical chamber 228. The first cam 232 can be biased by the first cam spring 256 against the cylindrical track 230, in the locked configuration. The second cam 234 can be biased by the second cam spring 258 against the cylindrical track 230, in the locked configuration.

As shown in FIGS. 43-46, the first attachment member 202 may be connected to the second attachment member 204. The first connection portion 206 is connected or integrally formed with the first attachment member 202. The first connection portion 206 and the first attachment member 202 can be aligned with a socket 800. Any changes in the orientation of the joint 200 changes the angle of the second attachment member 204 relative to the first attachment member 202. Further, any changes in the orientation of the joint 200 changes the angle of the prosthetic foot 700 attached to the second attachment member 204 relative to the socket 800 attached to the first attachment member 202. By changing the orientation of the joint 200, the prosthetic foot 700 can be inclined upward or downward relative to the ground. The ability to change the inclination of the prosthetic foot 700 may be helpful to adjust the orientation of the prosthetic foot 700, therefore allowing the user to adjust the operation (e.g., amount of compression, point of contact) of the prosthetic foot. Further, the ability to change the inclination of the prosthetic foot 700 may be useful, for example, when a user is walking up or down a constant grade.

As described above with respect to FIGS. 9-14, in the unlocked configuration, the axle 236, the first cam 232, the second cam 234, the first cam spring 256, and the second cam spring 258 can be rotated within the cylindrical track 230. The first attachment member 202 and the second attachment member 204 can rotate with respect to each other. The orientation of the prosthetic foot 700 connected to the first attachment member 202 relative to the socket 800 connected to the second attachment member 204 may affect the performance of the prosthetic device.

Figure 43:
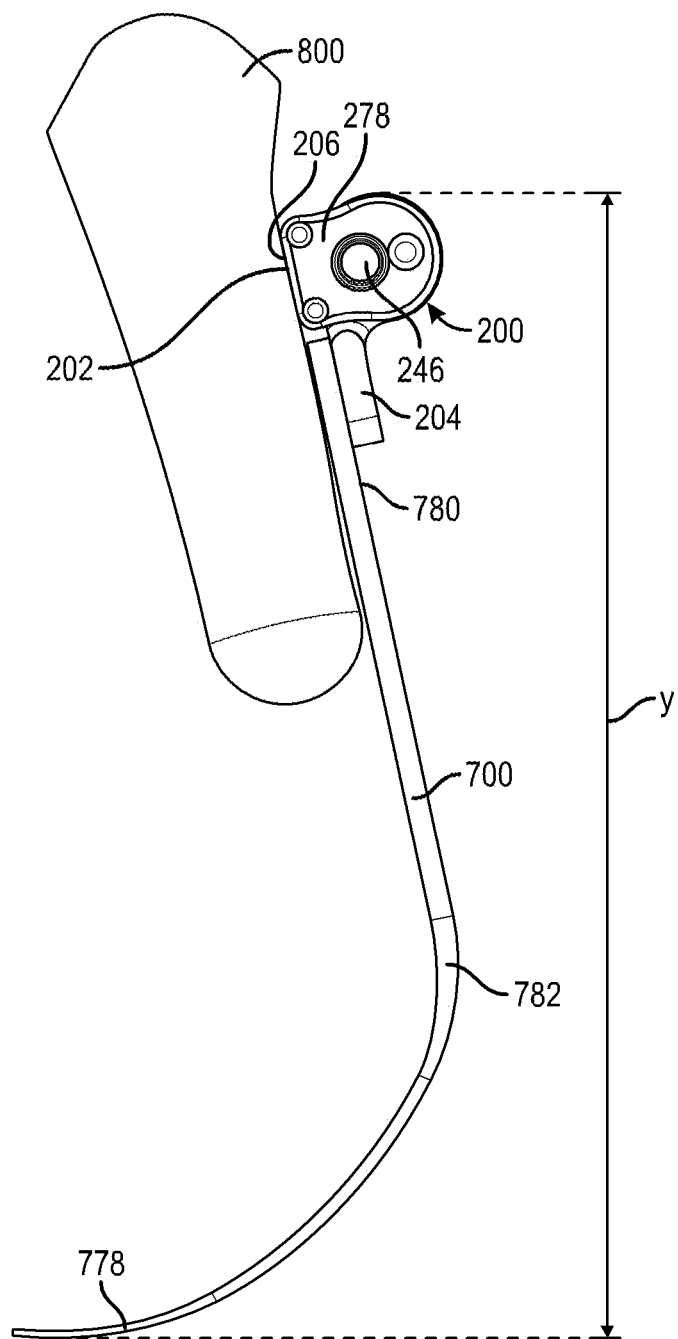
FIG. 43 is an embodiment of a prosthetic foot with a prosthetic joint of FIG. 9.

As shown in FIG. 43, the prosthetic foot 700 can include a toe portion 778 and a proximal portion 780. In some embodiments, the prosthetic foot 700 can include a first plate 782. The first plate 782 can form the planar contacting surface of the prosthetic foot 700. The first plate 782 can be curved as shown in FIGS. 43-46.

The second connection portion 208 of the second attachment member 204 can be couple to the first plate 782. In some embodiments, the second attachment member 204 is located near the proximal portion 780. In some embodiments, The first attachment member 202 is rigidly coupled to the socket 800. In some embodiments, the second attachment member 204 is rigidly coupled to the prosthetic foot 700. This allows the user to rotate the prosthetic foot 700 relative to the socket 800 to adjust the heel height.

In the unlocked configuration, the first attachment member 202 and the second attachment member 204 can rotate relative to each other. The prosthetic foot 700 moves as a unit with the second attachment member 204. When the desired orientation is reached, the prosthetic joint 200 can be locked. The first attachment member 202 remains fixed to the socket 800 in both the unlocked and locked configuration. The second attachment member 204 remains fixed to the prosthetic foot 700 in both the unlocked and locked configuration. The angular position of the toe portion 778 can be adjusted relative to the socket 800 based on the angle of rotation of the first attachment member 202 and the second attachment member 204.

Figure 44:
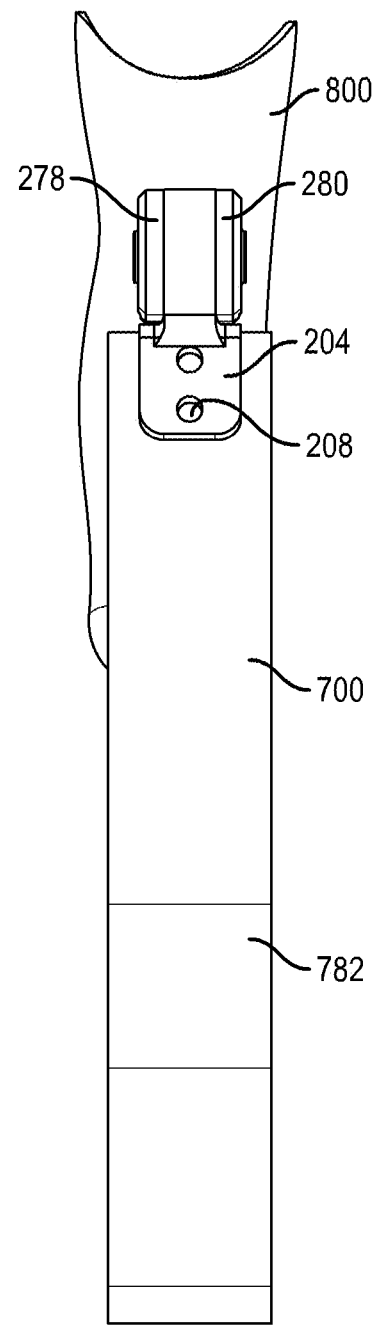
FIG. 44 is a rear view of the prosthetic foot of FIG. 43.
Figure 45:
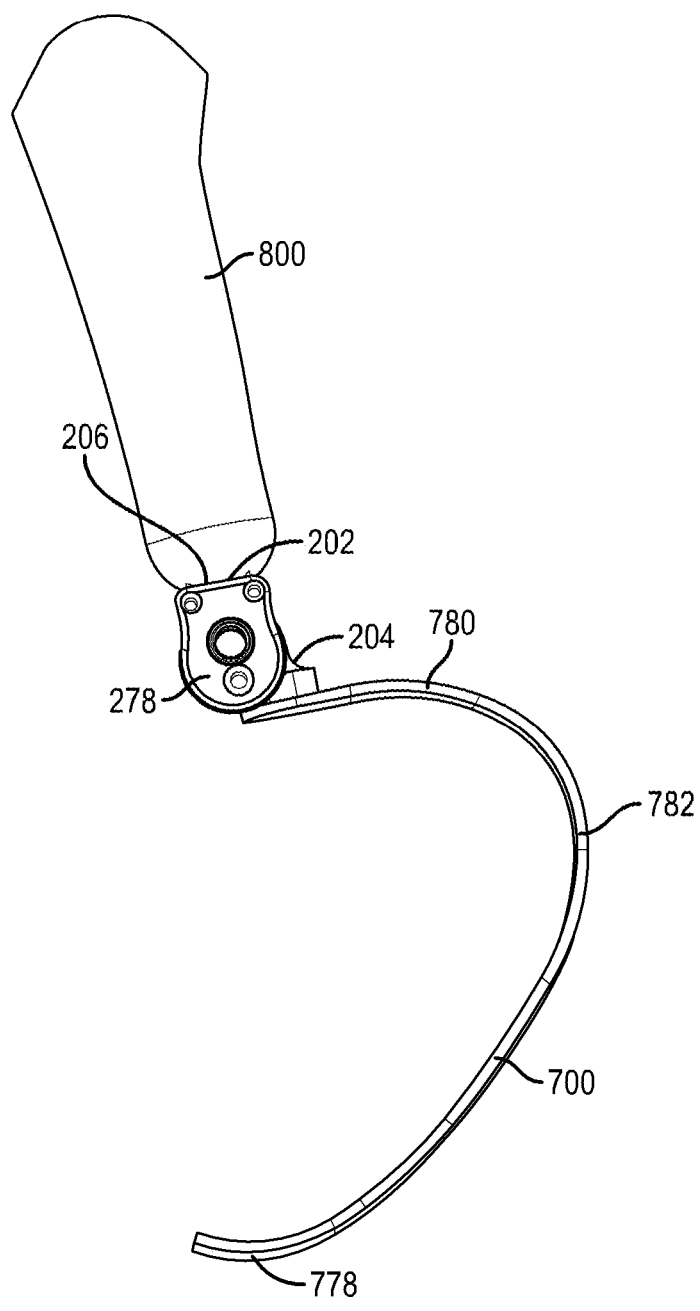
FIG. 45 is an embodiment of a prosthetic foot with a prosthetic joint of FIG. 9.
Figure 46:
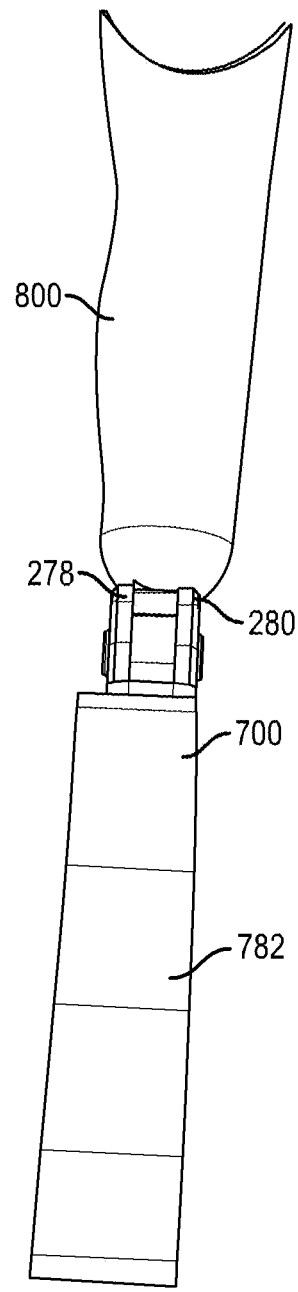
FIG. 46 is a rear view of the prosthetic foot of FIG. 45.

The axle 236 can be positioned in a range of circumferential locations relative to the cylindrical track 230. There is one position where the heel height is a maximum. The maximum position is shown in FIGS. 43-44. In this maximum position, the second attachment member 204 is rotated furthest away from the axle 236. Rotating the first attachment member 202 and the second attachment member 204 to a position other than the maximum position causes the heel height to decrease. The maximum position is shown in FIGS. 45-46 for a different system. In this maximum position, the second attachment member 204 is rotated 180 degrees form the first attachment member 202. Rotating the first attachment member 202 and the second attachment member 204 to a position other than the maximum position causes the heel height to decrease. The maximum position will depend on the orientation of the first attachment member 202 relative to the socket 800. The maximum position will depend on the orientation of the second attachment member 204 relative to the prosthetic foot 700.

In the range of circumferential locations, the socket 800 remains in a vertical position. The first connection portion 206 generally extends along an axis substantially perpendicular to the contact surface of the toe portion 778. The range of circumferential location is limited by the geometry of the system. In some embodiments, the range of locations is limited by the orientation of the first distally extending lid 278 and the second distally extending lid 280 with respect to the first attachment member 202. In some embodiments, the range of locations is limited by the orientation of the curved, concave inner surface 220 of the first attachment member 202 and the curved, convex outer surface 222 of the second attachment member 204. In some embodiments, the range of locations is limited by the abutment of the socket 800 with the prosthetic foot 700, as shown in FIG. 43.

Typically, the user of the prosthetic device adjusts the prosthetic joint 200 by utilizing the positioning members 246, 248. By depressing the positioning members 246, 248 the prosthetic joint changes from the locked configuration to the unlocked configuration, as described herein. In other embodiments, the turnkey 378, the lever 488, the linear member 586 or other positioning member can be utilized. In some embodiment, a manufacturer provides the prosthetic joint 200 and instruction of use. The instructions of use can describe how the user can adjust the prosthetic joint 200.

In some embodiments, the manufacture provides instructions for use of the system including one or more of the following steps, or any step previously described or inherent in the drawings. The steps may include: providing a first cam; providing a second cam; providing a first cam spring; providing a second cam spring; providing a first attachment member; providing a second attachment member; providing a cylindrical chamber; and/or providing a second attachment member having a cylindrical chamber.

The steps may include: coupling the first attachment member to the second attachment member; freely rotating the first attachment member with respect to the second attachment member; and/or locking in rotation the first attachment member with respect to the second attachment member. The steps may include: coupling a first distally extending arm with an axle, coupling a second distally extending arm with the axle; coupling the first cam with the axle; and/or coupling the second cam with the axle. The steps may include: coupling a first distally extending lid with an axle, coupling a second distally extending lid with the axle; coupling the first cam with the axle; and/or coupling the second cam with the axle.

The step may include biasing the first cam away from the second cam; biasing the first cam in a first direction; biasing the second cam in a second direction, wherein the second direction may be opposite the first direction; biasing the first cam with a first cam spring; and/or biasing the second cam with the second cam spring. The steps may include: contacting the first cam with a cylindrical track; contacting the first cam with a cylindrical chamber; contacting a second cam with the cylindrical track; contacting the second cam with the cylindrical chamber; preventing rotation in a first direction; and/or preventing rotation in a second direction, opposite the first direction.

The step may include aligning the first cam with the second cam; depressing a positioning member to align the first cam with the second cam; moving a lever to align the first cam with the second cam; rotating a turnkey to align the first cam with the second cam and/or pulling a brake wire to align the first cam with the second cam. The step may include overcoming a biasing force of a spring. The step may include biasing the first cam out of alignment with the second cam; releasing a positioning member to bias the first cam out of alignment with the second cam; moving a lever to bias the first cam out of alignment with the second cam; rotating a turnkey to bias the first cam out of alignment with the second cam and/or pulling a brake wire bias the first cam out of alignment with the second cam. The step may include preventing rotation of the first attachment member with respect to the second attachment member.

As discussed above with respect to the positioning members 146, 148, 246, 248, the turnkey 378, the positioning lever 488, and the linear member 586, the variable height control can be adjusted by the user. In some embodiments, the variable height control can be automatically or actively adjusted by the user. For instance, the first cam 132 can be aligned with the second cam 134 automatically. For instance, the first cam spring 156 can be actively varied. The automatic adjustment can be based on the activity level of the user, the gait cycle and/or the phase of gait cycle.

One example for an automatic mechanism is to have a magnetic pendulum in the cylindrical chamber 128 disposed between the first cam 132 and the second cam 134. In the absence of an applied magnetic field, the pendulum is in a first position (for instance, due to gravity or some other force). In the first position, the pendulum holds the first cam 132 and the second cam 134 apart so that they are not aligned. In other words, in the absence of an applied magnetic field, the prosthetic joint 100 is in the locked configuration. The first cam 132 is prevented from rotating with respect to the second cam 134. In the presence of an applied magnetic field, the pendulum is in a second position. In the second position, the pendulum aligns the first cam 132 and the second cam 134. The first attachment member 102 can rotate with respect to the second attachment member 104. In other embodiments, the first position aligns the first cam 132 and the second cam 134 and the second position holds the two cams apart.

In some embodiments the variable height control can be automatically adjusted based on a sensed parameter. In some embodiments the first attachment member, the second attachment member, and/or the attached prosthetic device such as the prosthetic foot 600, 700 and the socket 800 can include other features such as sensors configured to measure, for example, the position (e.g., angular position or angle) and movement of the prosthetic joint 100, 200, 300, 400, 500 and an attached prosthetic device, the position and movement of various joints and components on the attached prosthetic device (such as the rotational position and movement, as further discussed below), pressures and forces on various components of the prosthetic joint 100, 200, 300, 400, 500 and the attached prosthetic device (such as on the attachment member, or the actuator, further discussed below), and other measurable characteristics of the prosthetic joint 100, 200, 300, 400, 500 and the attached prosthetic device. The sensors can additionally be configured to measure the prosthetic joint's environment, such as a terrain on which the prosthetic joint 100, 200, 300, 400, 500 moves. It will be understood that these sensors can be positioned on other elements of the prosthetic joint 100, the attached prosthetic device, the actuator, and other elements, further described below.

The first attachment member the second attachment member or the attached prosthetic device can also include electronics (e.g., computer processor). For example, the first attachment member can include electronics configured to receive information from the sensors, discussed above. Further, in some embodiments, the first attachment member can include electronics configured to communicate information (e.g., information from the sensors) to other electronic devices, such as to other prosthetic devices or to an external computer (e.g., via wired or wireless communication, such as RF communication). Such electronics may also be configured to receive information from other prosthetic devices or an external computer, such information potentially including information from other sensors and/or operational commands for the prosthetic joint 100 and the attached prosthetic device.

The attachment member can additionally include or define a cover (not shown). The cover can protect various components of the prosthetic joint 100, 200, 300, 400, 500 such as electronics (as described above), the actuator (describe below), or other components. In some embodiments the cover can include open portions in the coronal plane, allowing flexibility of motion in the medial-lateral directions. In further embodiments the cover can include open portions in the sagittal plane, allowing flexibility of motion in the anterior-posterior directions.

The previous embodiments utilize a mechanical means to change from a locked configuration to an unlocked configuration. However, it is contemplated that the first attachment member can connect to an actuator (not shown). The actuator can be in a variety of forms and can be operated in a variety of ways, as described by way of example in U.S. patent application Ser. No. 11/367,049, issued Mar. 1, 2011 as U.S. Pat. No. 7,896,927, included herein as Appendix A, and U.S. patent application Ser. No. 12/816,968, published as U.S. 2010/0324698 on Dec. 23, 2010. For example, the actuator can be a powered actuator such as a screw motor, or a passive member such as an elastic member (e.g., a spring) or a chamber with a magnetorheologic fluid, or can be a hydraulic or pneumatic system. Further, the actuator can be configured to operate in a variety of ways, as also discussed in preceding patents.

The actuator can align the first cam and the second cam so that the prosthetic joint 100, 200, 300, 400, 500 is in the unlocked configuration. The actuator can rotate the first attachment member with respect to the second attachment member. The actuator can release the first cam and the second cam so that the prosthetic joint 100, 200, 300, 400, 500 is in the locked configuration.

In some embodiments, the actuator can also enter a low power mode (e.g., hibernation mode), such as a relaxed mode or an inactive mode. For example, the actuator may enter a low power mode during stance, as the embodiments described herein can provide greater stability during stance, as further described below. Advantageously, the low power mode allows for the conservation of battery power used to power the actuator, allowing the actuator to be operated for longer periods of time between battery charging.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. For example, the prosthetic joint and locking mechanism described herein can be incorporated into other prosthetic joints, such as a prosthetic hip joint, a prosthetic elbow joint, a prosthetic shoulder joint, etc., or into orthotic joints, such as an ankle orthosis or a knee and foot orthosis (KAFO). In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above.

Features, materials, characteristics, or groups described in conjunction with a particular aspect, embodiment, or example are to be understood to be applicable to any other aspect, embodiment or example described in this section or elsewhere in this specification unless incompatible there-with. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A prosthetic foot comprising:
a heel portion attached to a toe portion, wherein an angular position of the heel portion is adjustable relative to the toe portion;
a prosthetic joint comprising a first attachment member rotatably coupled with a second attachment member, wherein the second attachment member is connected with the heel portion and the first attachment member is configured to attach to a user or to another prosthetic device, wherein the prosthetic joint has an unlocked configuration that allows the first and second attachment members to rotate relative to each other and a locked configuration that inhibits the first and second attachment members from rotating relative to each other, and wherein the prosthetic joint comprises an axle; and
a connecting member extending from a proximal end to a distal end, wherein the proximal end is connected with the first attachment member and the distal end is connected with the toe portion, wherein the second attachment member comprises a cylindrical chamber defined about a first axis, and the axle is configured to extend along a second axis that is parallel and offset from the first axis.

2. The prosthetic foot of claim 1, wherein the proximal end of the connecting member is pivotally connected with the first attachment member and the distal end of the connecting member is pivotally connected with the toe portion.

3. The prosthetic foot of claim 1, wherein the first attachment member is configured to rotate relative to the second attachment member as the angular position of the heel portion relative to the toe portion is adjusted.

4. The prosthetic foot of claim 3, wherein the first attachment member is configured to rotate rearward relative to the second attachment member as the angular position of the heel portion relative to the toe portion is increased to increase the heel height.

5. The prosthetic foot of claim 1, wherein the heel portion is attached to the toe portion to form a prosthetic metatarsal joint.

6. The prosthetic foot of claim 1, wherein the connecting member comprises a spring component to bias the prosthetic joint towards either dorsiflexion or plantarflexion.

7. The prosthetic foot of claim 1, wherein the toe portion further comprises a first plate.

8. The prosthetic foot of claim 7, wherein the heel portion further comprises a second plate, wherein the first and second plates form one or more lower contacting surfaces.

9. The prosthetic foot of claim 8, wherein the first and second plates are separated at distal ends thereof.

10. The prosthetic foot of claim 1, wherein the second attachment member is fixedly attached to the heel portion.

11. The prosthetic foot of claim 1, wherein the prosthetic joint further comprises a cam and an actuator.

12. The prosthetic foot of claim 11, wherein the actuator is configured to rotate the cam about the second axis into or out of contact with the cylindrical chamber.

13. The prosthetic foot of claim 11, wherein in the unlocked configuration the actuator rotates the cam out of contact with the cylindrical chamber to thereby allow the first and second attachment members to rotate relative to each other, and wherein in the locked configuration the actuator rotates the cam into contact with the cylindrical chamber to thereby inhibit the first and second attachment members from rotating relative to each other.

14. The prosthetic foot of claim 11, wherein the actuator comprises a spring that biases the cam toward the locked configuration.

15. The prosthetic foot of claim 11, wherein the actuator comprises a button configured to engage and move the cam toward the unlocked configuration.

16. The prosthetic foot of claim 1, wherein the first attachment member is rotatably coupled to the second attachment member about the first axis, and wherein the prosthetic joint further comprises:

a fixation system disposed within the cylindrical chamber, the fixation system comprising at least one cam, at least one actuator, and the axle rotatably supporting the at least one cam that extends along the second axis that is parallel to and offset from the first axis, the at least one actuator configured to rotate the at least one cam about the second axis into or out of direct contact with the cylindrical chamber, and wherein the prosthetic joint is in the unlocked configuration when the at least one actuator rotates the at least one cam out of contact with the cylindrical chamber, and wherein the prosthetic joint is in the locked configuration when the at least one actuator rotates the at least one cam into contact with the cylindrical chamber.

17. The prosthetic foot of claim 16, wherein the at least one cam comprises a first cam and a second cam.

18. A prosthetic foot comprising:
a heel portion rotatably attached to a toe portion;
a prosthetic joint attached to the heel portion and comprising an axle and a rotatable first attachment member configured to be selectively locked in a plurality of rotated positions; and
a connecting member extending from the toe portion to the prosthetic joint,
wherein a height of the heel portion relative to the toe portion is adjustable, the second attachment member comprises a cylindrical chamber defined about a first axis, and the axle is configured to extend along a second axis that is parallel and offset from the first axis.

19. The prosthetic foot of claim 18, wherein the first attachment member is rotatably coupled with a second attachment member, wherein the second attachment member is connected with the heel portion and the first attachment member is configured to attach to a user or to another prosthetic device, and wherein the prosthetic joint has an unlocked configuration that allows the first and second attachment members to rotate relative to each other and a locked configuration that inhibits the first and second attachment members from rotating relative to each other.

20. The prosthetic foot of claim 18, wherein the prosthetic joint comprises a cam configured to be moved into and out of contact with a cylindrical chamber to thereby put the prosthetic joint respectively into a locked and an unlocked configuration.

* * * * *